(12) United States Patent
Apuya et al.

(10) Patent No.: US 7,312,376 B2
(45) Date of Patent: Dec. 25, 2007

(54) REGULATORY REGIONS FROM PAPAVERACEAE

(75) Inventors: Nestor Apuya, Culver City, CA (US); Yuping Lu, Camarillo, CA (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 11/360,017

(22) Filed: Feb. 22, 2006

(65) Prior Publication Data
US 2006/0265777 A1 Nov. 23, 2006

Related U.S. Application Data

(60) Provisional application No. 60/673,307, filed on Apr. 20, 2005.

(51) Int. Cl.
*C12N 15/82* (2006.01)
*C12N 5/04* (2006.01)
*A01H 5/00* (2006.01)
*A01H 5/10* (2006.01)

(52) U.S. Cl. .................. 800/278; 435/320.1; 435/419; 536/24.1; 800/295

(58) Field of Classification Search ...................... None
See application file for complete search history.

(56) References Cited

U.S. PATENT DOCUMENTS

| 4,654,465 A | 3/1987 | Brar et al. |
| 4,727,219 A | 2/1988 | Brar et al. |
| 4,801,340 A | 1/1989 | Inoue et al. |
| 4,801,540 A | 1/1989 | Hiatt et al. |
| 4,936,904 A | 6/1990 | Carlson |
| 4,946,778 A | 8/1990 | Ladner et al. |
| 4,987,071 A | 1/1991 | Cech et al. |
| 5,034,323 A | 7/1991 | Jorgensen et al. |
| 5,188,958 A | 2/1993 | Moloney et al. |
| 5,204,253 A | 4/1993 | Sanford et al. |
| 5,231,020 A | 7/1993 | Jorgensen et al. |
| 5,254,678 A | 10/1993 | Haseloff et al. |
| 5,283,184 A | 2/1994 | Jorgensen et al. |
| 5,380,831 A | 1/1995 | Adang et al. |
| 5,410,270 A | 4/1995 | Rybicki et al. |
| 5,432,068 A | 7/1995 | Albertsen et al. |
| 5,445,934 A | 8/1995 | Fodor et al. |
| 5,538,880 A | 7/1996 | Lundquist et al. |
| 5,723,766 A | 3/1998 | Theologis et al. |
| 5,766,847 A | 6/1998 | Jackle et al. |
| 5,777,079 A | 7/1998 | Tsien et al. |
| 5,824,779 A | 10/1998 | Koegel et al. |
| 5,824,798 A | 10/1998 | Tallberg et al. |

(Continued)

FOREIGN PATENT DOCUMENTS

EP      1 033 405      9/2000

(Continued)

OTHER PUBLICATIONS

Kim et al., (1994) A 20 nucleotide upstream element is essential for the nopaline synthase (nos) promoter activity. Plant Molecular Biology 24: 105-117.*

(Continued)

*Primary Examiner*—Anne Kubelik
*Assistant Examiner*—Brendan O. Baggot
(74) *Attorney, Agent, or Firm*—Fish & Richardson P.C.

(57) ABSTRACT

Regulatory regions suitable for regulating expression of a heterologous nucleic acid are described, as well as nucleic acid constructs that include these regulatory regions. Also disclosed are transgenic plants, e.g., *Papaveraceae* plants, that contain such constructs.

13 Claims, 6 Drawing Sheets taacttaattttcattagttcatggcagctagctagctaggctcctgttttcttatcttcatcaagaggtggtgatatactatgtgtatcttgactgtg
atatacaaattaaccatgagacacaagttaggtgggtaggtggacatgagctataggtggctaataaggcaagaaagggagatattttcttcg
atcaccaagggcgtaggtggctgggtcatgagctatagttggttttgataattcttcaatacgtgtggtccatgacattccttaggcaggatgat
ttggttggaaaactggctataacgctgccggtctttagtctaatgaacgtggcatgaaggatggttagtattgtggttagctcaattcagactctt
ttcactacatacgattgagaatggttggactttgtttggttttctcactcgctacgtctcagttgatgggtctaaggcctcttttcttttcgttttagact
aataaagttatctttatcgcgttctcattgtagattatgtaccaatgattatcttttctttctctctcttttgattatgtggtcttttgattatttgtctctcttt
aagatgagacaaataattgtagcccctttttttctgcataaatgcaatttgtcttgctaccattttcgaatggaactttaagatgagacaaataatt
attgagtggtatgagtctatatgatgttgacttcatcatggaccactccataccccaaaaactaacactatgatctaaagctatattaaaacggt
ttggttttgtggttagactaccagttcatcctctctatctcctcccaagaatatcaggtagct

U.S. PATENT DOCUMENTS

| | | | |
|---|---|---|---|
| 5,859,330 | A | 1/1999 | Bestwick et al. |
| 5,880,333 | A | 3/1999 | Goff et al. |
| 5,900,525 | A | 5/1999 | Austin-Phillips et al. |
| 5,925,806 | A | 7/1999 | McBride et al. |
| 5,958,745 | A | 9/1999 | Gruys et al. |
| 6,004,804 | A | 12/1999 | Kumar et al. |
| 6,010,907 | A | 1/2000 | Kmiec et al. |
| 6,013,863 | A | 1/2000 | Lundquist et al. |
| 6,087,558 | A | 7/2000 | Howard et al. |
| 6,136,320 | A | 10/2000 | Arntzen et al. |
| 6,255,562 | B1 | 7/2001 | Heyer et al. |
| 6,271,016 | B1 | 8/2001 | Anderson et al. |
| 6,294,717 | B1 | 9/2001 | Xie |
| 6,303,341 | B1 | 10/2001 | Hiatt et al. |
| 6,326,527 | B1 | 12/2001 | Kirihara et al. |
| 6,329,571 | B1 | 12/2001 | Hiei |
| 6,417,429 | B1 | 7/2002 | Hein et al. |
| 6,423,885 | B1 | 7/2002 | Waterhouse et al. |
| 6,452,067 | B1 | 9/2002 | Bedbrook et al. |
| 6,518,066 | B1 | 2/2003 | Oulmassov et al. |
| 6,573,099 | B2 | 6/2003 | Graham |
| 6,645,765 | B1 | 11/2003 | Anderson et al. |
| 6,664,446 | B2 | 12/2003 | Heard et al. |
| 6,706,470 | B2 | 3/2004 | Choo et al. |
| 6,753,139 | B1 | 6/2004 | Baulcombe et al. |
| 6,777,588 | B2 | 8/2004 | Waterhouse et al. |
| 6,835,540 | B2 | 12/2004 | Broun |
| 6,906,244 | B2 | 6/2005 | Fischer et al. |
| 2002/0023281 | A1 | 2/2002 | Gorlach et al. |
| 2002/0081731 | A1 | 6/2002 | Stafford et al. |
| 2003/0037355 | A1 | 2/2003 | Barbas et al. |
| 2003/0061637 | A1 | 3/2003 | Zhong et al. |
| 2003/0131386 | A1 | 7/2003 | Samaha et al. |
| 2003/0140381 | A1 | 7/2003 | Bate et al. |
| 2003/0153097 | A1 | 8/2003 | Deshaies et al. |
| 2003/0170656 | A1 | 9/2003 | Cen et al. |
| 2003/0175783 | A1 | 9/2003 | Waterhouse et al. |
| 2003/0175965 | A1 | 9/2003 | Lowe et al. |
| 2003/0180945 | A1 | 9/2003 | Wang et al. |
| 2003/0229915 | A1 | 12/2003 | Keddie et al. |
| 2004/0019927 | A1 | 1/2004 | Sherman et al. |
| 2004/0034888 | A1 | 2/2004 | Liu et al. |
| 2004/0045049 | A1 | 3/2004 | Zhang et al. |
| 2004/0053876 | A1 | 3/2004 | Turner et al. |
| 2004/0072159 | A1 | 4/2004 | Takaiwa et al. |
| 2004/0073972 | A1 | 4/2004 | Beachy et al. |
| 2004/0078852 | A1 | 4/2004 | Thomashow et al. |
| 2004/0203109 | A1 | 10/2004 | Lal et al. |
| 2004/0214330 | A1 | 10/2004 | Waterhouse et al. |
| 2004/0216190 | A1 | 10/2004 | Kovalic |
| 2005/0009187 | A1 | 1/2005 | Shinozaki et al. |
| 2005/0081261 | A1 | 4/2005 | Pennell et al. |
| 2005/0108791 | A1 | 5/2005 | Edgerton et al. |
| 2005/0223434 | A1 | 10/2005 | Alexandrov et al. |
| 2005/0246785 | A1 | 11/2005 | Zhihong et al. |
| 2005/0257293 | A1 | 11/2005 | Mascia |
| 2006/0015970 | A1 | 1/2006 | Pennell et al. |
| 2006/0143729 | A1 | 6/2006 | Alexandrov et al. |
| 2006/0194959 | A1 | 8/2006 | Alexandrov et al. |
| 2006/0195934 | A1 | 8/2006 | Apuya et al. |
| 2006/0272060 | A1 | 11/2006 | Heard et al. |
| 2007/0022495 | A1 | 1/2007 | Reuber et al. |

FOREIGN PATENT DOCUMENTS

| | | |
|---|---|---|
| WO | 99/34663 | 7/1999 |
| WO | 00/42200 | 7/2000 |
| WO | 00/46383 | 8/2000 |
| WO | 06/005023 | 1/2006 |

OTHER PUBLICATIONS

Hannenhalli et al., (2001) Promoter prediction in the human genome. Bioinformatics 17: S90-S96.*
Hauschild, et al (1998) Isolation and analysis of the gene bbe1 encoding the berberine bridge enzyme from the California poppy *Eschscholzia californica* Plant Molec. Biol. 36:473-478.*
U.S. Appl. No. 60/121,700, filed Feb. 25, 1999, Jofuku et al.
Allen et al. "RNAi-mediated replacement of morphine with the nonnarcotic alkaloid reticuline in opium poppy" *Nature Biotechnology*, 22(12):1559-1566 (2004).
Bird et al. "A tale of three cell types: alkaloid biosynthesis is localized to sieve elements in opium poppy" *The Plant Cell*, 15:2626-2635 (2003).
Chitty et al., "Genetic transformation in commercial Tasmanian cultures of opium poppy, Papaver somniferum, and movement of transgenic pollen in the field, " *Funct. Plant Biol.* 30:1045-1058 (2003).
Chou et al. "Enzymatic oxidation in the biosynthesis of complex alkaloids" *The Plant Journal*, 15(3):289-300 (1998).
Dr. Duke's Phytochemical and ethnobotanical databases, obtained from the Internet on Feb. 9, 2005 at http://www.ars-grin.gov/cgi-bin/duke/farmacy2.pl, 7 pages.
Facchini et al., "Expression patterns conferred by tyrosine/dihydroxyphenylalanine decarboxylase promoters from opium poppy are conserved in transgenic tobacco" *Plant Physiology, American Society of Plant Physiologists*, vol. 118(1):69-81 (1998).
Facchini "Alkaloid biosynthesis in plants: Biochemistry, cell biology, molecular regulation, and metabolic engineering applications" *Annu. Rev. Plant Physiol. Plant Mol. Biol.* 52:29-66 (2001).
Hannenhalli et al. "Promoter prediction in the human genome" *Bioinformatics*, 17:S90-S96 (2001).
Hauschild et al. "Isolation and analysis of the gene bbe1 encoding the berberine bridge enzyme from the California poppy *Eschscholzia californica*" *Plant Molec. Biol.* , 36:473-478 (1998).
Kutchan "Molecular genetics of plant alkaloid biosynthesis" *The Alkaloids*, 50:257-316 (1998).
Memelink "Putting the opium in poppy to sleep" *Nature Biotechnology*, 22(12):1526-1527 (2004).
Ounaroon et al. "(R, S)-Reticuline 7-O-methyltrasnferase and (R, S)-norcoclaurine 6-O-methyltransferase of *Papaver somniferum* -cDNA cloning and characterization of methyl transfer enzymes of alkaloid biosynthesis in opium poppy" *The Plant Journal*, 36(6):808-819 (2003).
Park et al., "Analysis of promoters from tyrosine/dihydroxyphenylalanine decarboxylase and berberine bridge enzyme genes involved in benzylisoquinoline alkaloid biosynthesis in opium poppy" *Plant Molecular Biology*, 40(1):121-131 (1999).
Park & Facchini, "High-efficiency somatic embryogenesis and plant regeneration in California poppy, *Eschscholzi califronica* Cham." *Plant Cell Rep.* 19:421-426, (2000).
Park et al., "Agrobacterium rhizogenes-mediated tranformation of opium poppy, *Papaver somniferum* L., and California poppy, *Eschscholzia californica* Cham., root cultures" *J. Exp. Botany*, 2000, 51(347):1005-1016.
Park & Facchini, "*Agrobacterium*-mediated genetic tranformation of California poppy, *Eschscholzia californica* Cham., via somatic embryogenesis" *Plant Cell Rep.* 19: 1006-1012, (2000).
Pasquali et al. "Coordinated regulation of two indole alkaloid biosynthetic genes from catharanthus-roseus by auxin and elicitors" *Plant Molecular Biology*, 18(16):1121-1131 (1992).
Potenza et al. "Invited review: Targeting transgene expression in research, agricultural, and environmental applications: Promoters used in plant transformation" *In Vitro Cellular and Developmental Biology*, 40(1):1-22 (2004).
Verpoorte et al. "Engineering secondary metabolite production in plants" *Current Opinion in Biotechnology*, 13(2):181-187 (2002).
Zhang et al. "Metabolic engineering of tropane alkaloid biosynthesis in plants" *Journal of Integrative Plant Biology*, 47(2):136-143 (2005).

* cited by examiner

Figure 1 taacttaatttttcattagttcatggcagctagctagctaggctcctgttttcttatcttcatcaagaggtggtgatatactatgtgtatcttgactgtg
atatacaaattaaccatgagacacaagttaggtgggtaggtggacatgagctataggtggctaataaggcaagaaagggagatattttcttcg
atcaccaagggcgtaggtggctgggtcatgagctatagttggtttttgataattcttcaatacgtgtggtccatgacattccttaggcaggatgat
ttggttggaaaactggctataacgctgccggtctttagtctaatgaacgtggcatgaaggatggttagtattgtggttagctcaattcagactctt
ttcactacatacgattgagaatggttggactttgtttggttttctcactcgctacgtctcagttgatgggtctaaggcctctttcttttcgttttagact
aataaagttatctttatcgcgttctcattgtagattatgtaccaatgattatctttttctttctctctcttttgattatgtggtcttttgattatttgtctctcttt
aagatgagacaaataattgtagcccctttttttttctgcataaatgcaatttgtcttgctaccatttttcgaatggaactttaagatgagacaaataatt
attgagtggtatgagtctatatgatgttgacttcatcatggaccactccatacccccaaaaactaacactatgatctaaagctatattaaaacggt
ttggttttgtggttagactaccagttcatcctctctatctcctcccaagaatatcaggtagct

Figure 2 ttaagtgttttagttttgttacaagtttggtgaatgatctttgatgatattttttttttgaagtagtgaacgaagtaatgttctacttcccataggatttgc
tctaacgattaactatgtttgtcccaaagggttgtatgacttacatacacaatattaaaagattcgaggataaggatatgtttattaaccaactcct
caaaacatttagacctggatcaatcagttcgattcttctcagacaattacgacatgtatgaatcgatggatacatttgaaacatatatccttaccc
gtgccgttacggcatgggttgagacctagtgattacatataaaacaactaattataccaatgacttgagttcgaaactcgtcccatgatcaatttt
ttatcaatcaaaagaaatttatacgaaaggaaactatatgattgccatgactcgtaaatatacacaagcaatatggaggtcctattaactccaat
caaaccacaatagataaatatatcgtgaatcatgtgtggccaatatatacccacacttctatatataagtgcatccacttctctttgttttccaaaac
aaaacataaacacaatttattcaga

Figure 3 agcacagaaaaaagcccttgctctttcatgtagcatattattaattaagcttgtcaattttcagtcttatgttttgaagcatattggctgagattttatt
atgtgcttgactgggttttccaggaaattaccactggcaggtcaatcaagaattttctcagaacttaaacttccggcccggcagatgcaagaa
aacacatataccacttgcatgaaaccagatatagcatgggctgacctttctcagaattattcccacgagcttcttgcttttctctcgtgggctgat
gatatatgtgacactcctcaacagcaaccgccactgtcaacaactttagtactataccaacttataatgatttcttagttaggtcatggtggggga
cttattcttttctttttttttttgttgaatattcatatctgcatcctttaatgcacacaaacggtccggcaggcttagctgcatgcacttataaatacacca
taaattttgaagagatttcaaaacacccacacataacccaaagccaaagcaaaaaactgtcttctcttcttgacaattatatacagc

Figure 4 ttgtcgagagagatgaattacaaaacaaaatagaaagcatcagcatattacattattacatcgatcctttataaaagataatatatacatacatat
atatatatatatatataacctttggtcttcaactgctattgaattacaaaacaaaatagaaagcatcagcatattacatcgatcctttattcggaaag
aggggtattctgttcggtgagagtttcttcttatccagctcctcgcaaatgaaatgattccataatacctctctaaaagacttggtcattatataag
agagggagaccacgagcttcttctaaacaacagaaagtatcatctaccattatcaatcctgttaaacagttaaacactttgg

Figure 5 caatgccaatgcgtgacatcacctactagtagaggcatcaaagccaatatcattatctcacaatgtcaatagatgcccacgattggcatcatca
gttgaagcgccacttaatgctcagatctacttgtcaaaatttgacatggatttagtcaagtacatattccactttatcaagtctctaataaacttgcg
ggtgtcgcgagggttgacactaattagtctagttaattattgcagtgtactgaaccttgactcaatcgcttttccaaggaagtctccgtttgaatta
atcgacttaacagtaacaacactttattttactattgttatttatacgagatatcaataatgtcccatggagaatatctttagggttttagtctggcagt
ttacagcatttatagatgtcgtagaacatttacttgcaacatgaaaaagaagttagctgtggaatattataggtcagtcgacctattgataagacg
gtattgataagacggacaaatcttatacgattgtagtttcacatgcttcatattacttgaaccacaatgatagacattatctcaataaccgcatagc
tttacatacttccgcttgaatcctaacactccgatctcgctctttatccgtttctgttcctaagaccaattctcctcctcctattgtgaccagagcaat
accgtggtcgaaaatcttcatcagcatctagaattttcctcctgaccgaataccaacacggtaacctgaaatgtaattcataatccaaaatttgc
attatgagtacccttgacctaaaatctcctttgtaattcaaaatattggtcactacataaaatcgtctcctgtaactctaaatatttcatcaagatcca
cagtgctccttatgaagcaaagtgtacttaatggctcaaaatattcatgtggttcaaaatctatcttgcgcgcacaacagtcatgtgacacaa

Figure 6 ctgtcataaagaggtctggttcgcataatgtgctctgctaactccagaatttgattgtgcaccaccaaactcattaagtaaaaattacagaatca
agatgtacactatgttttgggagttatgattattgaaagataaaaagttgaattactaaacagaatggctttagtgactaatctaatttctgatagat
aatgctctagcattagttatctaatatgacttccactaaaatccctttgtatcttcgctttccagatcggatcattgcgaatcgtggatcctttccat
aagtgcattctttttttataaaaaaaaatgacaatacaaatccctaataatcaatcataattatatagagcgaaatacaatgttctcaacttgggga
gcttccctagtgctaaagagggcctatgttttgtccagctacttatcaaagatatccaaatcctcagaagatttatattttgtttggttagcttatat
gaccaaaccctaagacaggaaagtccgattaagaggggtcataccttcataatcttgattatcatctgtttattcttgtttcttgtttctactgtctaa
tagaactgaatgacaactcttttgtggctggcacagttgcaggcatgttatgcttttgtctcatctagattactttatttattttttgaagcatatttaa
tttatagaatacataatatctaaactaaattactttataattacgtatttgtagcttggttaagatttctaatctttattttaatttaatattatttcctattaa
aaaactgatttgttgactaaaaataattttaatgtcgtttaacataggtataaattatataactatactctatacctgctcccccgtgctactcttttga
ccacctatcttactgcagtttgcccgattgagag

SEQUENCE LISTING

<160> NUMBER OF SEQ ID NOS: 34

<210> SEQ ID NO 1
<211> LENGTH: 850
<212> TYPE: DNA
<213> ORGANISM: Eschscholzia californica
<220> FEATURE:
<221> NAME/KEY: misc_feature
<222> LOCATION: (1)..(850)
<223> OTHER INFORMATION: EcNMCH3

<400> SEQUENCE: 1

```
taacttaatt tttcattagt tcatggcagc tagctagcta ggctcctgtt ttcttatctt      60
catcaagagg tggtgatata ctatgtgtat cttgactgtg atatacaaat taaccatgag     120
acacaagtta ggtgggtagg tggacatgag ctataggtgg ctaataaggc aagaaaggga     180
gatattttct tcgatcacca agggcgtagg tggctgggtc atgagctata gttggttttt     240
gataattctt caatacgtgt ggtccatgac attccttagg caggatgatt tggttggaaa     300
actggctata acgctgccgg tctttagtct aatgaacgtg gcatgaagga tggttagtat     360
tgtggttagc tcaattcaga ctcttttcac tacatacgat tgagaatggt tggactttgt     420
ttggttttct cactcgctac gtctcagttg atgggtctaa ggcctctttc ttttcgtttt     480
agactaataa agttatcttt atcgcgttct cattgtagat tatgtaccaa tgattatctt     540
tttctttctc tctcttttga ttatgtggtc ttttgattat ttgtctctct ttaagatgag     600
acaaataatt gtagccccctt tttttctgc ataaatgcaa tttgtcttgc taccattttt     660
cgaatggaac tttaagatga gacaaataat tattgagtgg tatgagtcta tatgatgttg     720
acttcatcat ggaccactcc atacccccaa aaactaacac tatgatctaa agctatatta     780
aaacggtttg gttttgtggt tagactacca gttcatcctc tctatctcct cccaagaata     840
tcaggtagct                                                           850
```

<210> SEQ ID NO 2
<211> LENGTH: 610
<212> TYPE: DNA
<213> ORGANISM: Papaver somniferum
<220> FEATURE:
<221> NAME/KEY: misc_feature
<222> LOCATION: (1)..(610)
<223> OTHER INFORMATION: PsROMT

<400> SEQUENCE: 2

```
ttaagtgttt ttagttttgt tacaagtttg gtgaatgatc tttgatgata tttttttttt      60
gaagtagtga acgaagtaat gttctacttc ccataggatt tgctctaacg attaactatg     120
tttgtcccaa agggttgtat gacttacata cacaatatta aaagattcga ggataaggat     180
atgttattta accaactcct caaaacattt agacctggat caatcagttc gattcttctc     240
agacaattac gacatgtatg aatcgatgga tacatttgaa acatatatcc ttacccgtgc     300
cgttacggca tgggttgaga cctagtgatt acatataaaa caactaatta taccaatgac     360
ttgagttcga aactcgtccc atgatcaatt tttatcaat caaagaaat ttatacgaaa       420
ggaaactata tgattgccat gactcgtaaa tatacacaag caatatggag gtcctattaa     480
ctccaatcaa accacaatag ataaatatat cgtgaatcat gtgtggccaa tatatcccca    540
cacttctata tataagtgca tccacttctc tttgttttcc aaaacaaaac ataaacacaa     600
tttattcaga                                                           610
```

<210> SEQ ID NO 3
<211> LENGTH: 575
<212> TYPE: DNA
<213> ORGANISM: Papaver somniferum
<220> FEATURE:
<221> NAME/KEY: misc_feature
<222> LOCATION: (1)..(575)
<223> OTHER INFORMATION: PsHMCOMT2

<400> SEQUENCE: 3

| | | | | | |
|---|---|---|---|---|---|
| agcacagaaa | aaagcccttg | ctctttcatg | tagcatatta | ttaattaagc | ttgtcaattt | 60 |
| tcagtcttat | gttttgaagc | atattggctg | agatttttat | tatgtgcttg | actgggtttt | 120 |
| ccaggaaatt | accactggca | ggtcaatcaa | gaattttct | cagaacttaa | acttccggcc | 180 |
| cggcagatgc | aagaaaacac | ataccact | tgcatgaaac | cagatatagc | atgggctgac | 240 |
| ctttctcaga | attattccca | cgagcttctt | gcttttctct | cgtgggctga | tgatatatgt | 300 |
| gacactcctc | aacagcaacc | gccactgtca | acaactttag | tactatacca | acttataatg | 360 |
| atttcttagt | taggtcatgg | tgggggactt | attcttttct | tttttttg | ttgaatattc | 420 |
| atatctgcat | cctttaatgc | acacaaacgg | tccggcaggc | ttagctgcat | gcacttataa | 480 |
| atacaccata | aattttgaag | agatttcaaa | acacccacac | ataacccaaa | gccaaagcaa | 540 |
| aaaactgtct | tctcttcttg | acaattatat | acagc | | | 575 |

<210> SEQ ID NO 4
<211> LENGTH: 373
<212> TYPE: DNA
<213> ORGANISM: Papaver somniferum
<220> FEATURE:
<221> NAME/KEY: misc_feature
<222> LOCATION: (1)..(373)
<223> OTHER INFORMATION: PsSAT

<400> SEQUENCE: 4

| | | | | | |
|---|---|---|---|---|---|
| ttgtcgagag | agatgaatta | caaaacaaaa | tagaaagcat | cagcatatta | cattattaca | 60 |
| tcgatccttt | ataaaagata | atatatacat | acatatatat | atatatatat | ataaccttg | 120 |
| gtcttcaact | gctattgaat | tacaaaacaa | aatagaaagc | atcagcatat | tacatcgatc | 180 |
| ctttattcgg | aaagaggggt | attctgttcg | gtgagagttt | cttcttatcc | agctcctcgc | 240 |
| aaatgaaatg | attccataat | acctctctaa | aagacttggt | cattatataa | gagagggaga | 300 |
| ccacgagctt | cttctaaaca | acagaaagta | tcatctacca | ttatcaatcc | tgttaaacag | 360 |
| ttaaacactt | tgg | | | | | 373 |

<210> SEQ ID NO 5
<211> LENGTH: 968
<212> TYPE: DNA
<213> ORGANISM: Papaver somniferum
<220> FEATURE:
<221> NAME/KEY: misc_feature
<222> LOCATION: (1)..(968)
<223> OTHER INFORMATION: PsCRX

<400> SEQUENCE: 5

| | | | | | |
|---|---|---|---|---|---|
| caatgccaat | gcgtgacatc | acctactagt | agaggcatca | agccaatat | cattatctca | 60 |
| caatgtcaat | agatgcccac | gattggcatc | atcagttgaa | gcgccactta | atgctcagat | 120 |
| ctacttgtca | aaatttgaca | tggatttagt | caagtacata | ttccactta | tcaagtctct | 180 |
| aataaacttg | cgggtgtcgc | gagggttgac | actaattagt | ctagttaatt | attgcagtgt | 240 |

```
actgaacctt gactcaatcg cttttccaag gaagtctccg tttgaattaa tcgacttaac    300
agtaacaaca ctttatttta ctattgttat ttatacgaga tatcaataat gtcccatgga    360
gaatatcttt agggttttag tctggcagtt tacagcattt atagatgtcg tagaacattt    420
acttgcaaca tgaaaagaa gttagctgtg gaatattata ggtcagtcga cctattgata     480
agacggtatt gataagacgg acaaatctta tacgattgta gtttcacatg cttcatatta    540
cttgaaccac aatgatagac attatctcaa taaccgcata gctttacata cttccgcttg    600
aatcctaaca ctccgatctc gctctttatc cgtttctgtt cctaagacca attctcctcc    660
tcctattgtg accagagcaa taccgtggtc gaaaatcttc atcagcatct agaattttcc    720
tcctgaccga ataccaacac ggtaacctga aatgtaattc ataatccaaa atttgcatta    780
tgagtaccct tgacctaaaa tctcctttgt aattcaaaat attggtcact acataaaatc    840
gtctcctgta actctaaata tttcatcaag atccacagtg ctccttatga agcaaagtgt    900
acttaatggc tcaaaatatt catgtggttc aaaatctatc ttgcgcgcac aacagtcatg    960
tgacacaa                                                            968
```

```
<210> SEQ ID NO 6
<211> LENGTH: 930
<212> TYPE: DNA
<213> ORGANISM: Papaver somniferum
<220> FEATURE:
<221> NAME/KEY: misc_feature
<222> LOCATION: (1)..(930)
<223> OTHER INFORMATION: PsCR3

<400> SEQUENCE: 6
```

```
ctgtcataaa gaggtctggt tcgcataatg tgctctgcta actccagaat ttgattgtgc     60
accaccaaac tcattaagta aaaattacag aatcaagatg tacactatgt tttgggagtt    120
atgattattg aaagataaaa agttgaatta ctaaacagaa tggctttagt gactaatcta    180
atttctgata gataatgctc tagcattagt tatctaatat gacttccact aaaatcccct    240
tgtatcttcg ctttccagat cggatcattg cgaatcgtgg atccttttcc ataagtgcat    300
tcttttttta taaaaaaaa tgacaataca aatccctaat aatcaatcat aatttatatag    360 agcgaaatac aatgttctca acttggggag cttccctagt gctaaagagg gcctatgttt    420
tgtccagcta cttatcaaag atatccaaat cctcagaaga tttatatttt tgtttggtta    480
gcttatatga ccaaacccta agacaggaaa gtccgattaa gagggtcat  accttcataa     540 tcttgattat catctgttta ttcttgtttc ttgtttctac tgtctaatag aactgaatga    600
caactctttt tgtggctggc acagttgcag gcatgttatg cttttgtctc atctagatta    660
ctttatttta tttttttgaag catatttaat ttatagaata cataatatct aaactaaatt    720
actttataat tacgtatttg tagcttggtt aagatttcta atcttttatt ttaatttaat    780
attatttcct attaaaaaac tgattgttg actaaaaata attttaatgt cgtttaacat    840
aggtataaat tatataacta tactctatac ctgctccccc gtgctactct ttttgaccac    900
ctatcttact gcagtttgcc cgattgagag                                     930
```

```
<210> SEQ ID NO 7
<211> LENGTH: 272
<212> TYPE: PRT
<213> ORGANISM: Arabidopsis thaliana
<220> FEATURE:
<221> NAME/KEY: MISC_FEATURE
<222> LOCATION: (1)..(272)
<223> OTHER INFORMATION: Ceres GEMINI ID 531H6
```

```
<220> FEATURE:
<221> NAME/KEY: MISC_FEATURE
<222> LOCATION: (1)..(272)
<223> OTHER INFORMATION: Ceres CLONE ID 40501
<220> FEATURE:
<221> NAME/KEY: MISC_FEATURE
<222> LOCATION: (1)..(272)
<223> OTHER INFORMATION: Ceres CDNA ID no. 23427553

<400> SEQUENCE: 7

Met Ser Met Ser Gln Ser Arg Ala Val Gln Arg Ser Ser Pro Asn
1               5                   10                  15

Glu Asp Arg Gly Glu Asn Gln Leu Val Val Tyr Asp Leu Lys Gly Asn
            20                  25                  30

Asp Asp Thr Glu Glu Val Leu Pro Val Gln Ser Gln Pro Leu Ser
        35                  40                  45

Ser Arg Thr Gln Cys Pro Ser Ile Gly Ala Phe Thr Val Gln Cys Ala
    50                  55                  60

Ser Cys Phe Lys Trp Arg Leu Met Pro Ser Met Gln Lys Tyr Glu Glu
65                  70                  75                  80

Ile Arg Glu Gln Leu Leu Glu Asn Pro Phe Phe Cys Asp Thr Ala Arg
                85                  90                  95

Glu Trp Lys Pro Asp Ile Ser Cys Asp Val Pro Ala Asp Ile Tyr Gln
            100                 105                 110

Asp Gly Thr Arg Leu Trp Ala Ile Asp Lys Pro Asn Ile Ser Arg Pro
        115                 120                 125

Pro Ala Gly Trp Gln Arg Leu Leu Arg Ile Arg Gly Glu Gly Gly Thr
    130                 135                 140

Arg Phe Ala Asp Val Tyr Tyr Val Ala Pro Ser Gly Lys Lys Leu Arg
145                 150                 155                 160

Ser Thr Val Glu Val Gln Lys Tyr Leu Asn Asp Asn Ser Glu Tyr Ile
                165                 170                 175

Gly Glu Gly Val Lys Leu Ser Gln Phe Ser Phe Gln Ile Pro Lys Pro
            180                 185                 190

Leu Gln Asp Asp Tyr Val Arg Lys Arg Pro Ala Arg Leu Leu Asp Ser
        195                 200                 205

Ile Asp Asn Thr Asn Thr Pro Val Ala Lys Glu Ala Asn Pro Leu Ala
    210                 215                 220

Trp Ile Ser Pro Asp Asp His Ile Ser Leu Gln Leu Gly Thr Pro Thr
225                 230                 235                 240

Glu Ser Gly Leu Asn Asn Ser His Tyr Gln Pro Ser Lys Lys Lys Lys
                245                 250                 255

Thr Ser Thr Leu Ser Ile Phe Gly Ser Asn Asp Glu Leu Ala Asp Arg
            260                 265                 270

<210> SEQ ID NO 8
<211> LENGTH: 202
<212> TYPE: PRT
<213> ORGANISM: Glycine max
<220> FEATURE:
<221> NAME/KEY: MISC_FEATURE
<222> LOCATION: (1)..(202)
<223> OTHER INFORMATION: Ceres GEMINI ID 531G11
<220> FEATURE:
<221> NAME/KEY: MISC_FEATURE
<222> LOCATION: (1)..(202)
<223> OTHER INFORMATION: Ceres CLONE ID 605218
<220> FEATURE:
<221> NAME/KEY: MISC_FEATURE
<222> LOCATION: (1)..(202)
<223> OTHER INFORMATION: Ceres CDNA ID no. 23395214
```

```
<400> SEQUENCE: 8

Met Val Ser Ala Thr Val Asp Ser Asp Phe Ala Phe Leu Glu Ser Val
1               5                   10                  15

Gln Gln Tyr Leu Leu Gly His Asp Ser Ile Asn Leu Met Ser Glu Thr
            20                  25                  30

His Gln Ala Ala Ser His Asp Pro Phe Ser Asp Pro Asn Lys Cys Asp
        35                  40                  45

Gly Asp Ser Gly Asn Ile Ala Phe Arg Ser Glu Asp Ala Thr Ala Val
    50                  55                  60

Val Ala Arg Asp His Ala Pro Pro Thr Trp Lys His Tyr Arg Gly Val
65                  70                  75                  80

Arg Arg Arg Pro Trp Gly Lys Phe Ala Ala Glu Ile Arg Asp Pro Lys
                85                  90                  95

Lys Asn Gly Ala Arg Val Trp Leu Gly Thr Tyr Asp Thr Glu Glu Lys
            100                 105                 110

Ala Ala Leu Ala Tyr Asp Lys Ala Ala Phe Lys Met Arg Gly Gln Lys
        115                 120                 125

Ala Lys Leu Asn Phe Pro His Leu Ile Asp Ser Asp Asn Ser Asp Glu
    130                 135                 140

Leu Ser Glu Pro Val Met Met Thr Thr Ser Lys Arg Ser Leu Leu Glu
145                 150                 155                 160

Ile Ser Ser Pro Ser Ser Cys Ser Asp Asp Ser Ser Glu Ser Ser Gln
                165                 170                 175

Gly Thr Lys Arg Arg Lys Ser Leu Ala Glu Leu Leu Asn Lys Leu Ala
            180                 185                 190

Lys Asn Arg Ser Gln Val Lys Val Glu Cys
            195                 200

<210> SEQ ID NO 9
<211> LENGTH: 204
<212> TYPE: PRT
<213> ORGANISM: Arabidopsis thaliana
<220> FEATURE:
<221> NAME/KEY: MISC_FEATURE
<222> LOCATION: (1)..(204)
<223> OTHER INFORMATION: Ceres GEMINI ID 531H9
<220> FEATURE:
<221> NAME/KEY: MISC_FEATURE
<222> LOCATION: (1)..(204)
<223> OTHER INFORMATION: Ceres CLONE ID 21374
<220> FEATURE:
<221> NAME/KEY: MISC_FEATURE
<222> LOCATION: (1)..(204)
<223> OTHER INFORMATION: Ceres CDNA ID no. 23447935

<400> SEQUENCE: 9

Met Leu Pro Phe Pro Ala Met Asn Leu Lys Lys Ser Arg Ser Glu Asn
1               5                   10                  15

Ser Ser Val Ala Ser Ser Gly Ser Lys Ile Glu Glu Gln Thr Glu Lys
            20                  25                  30

Ser Ala Glu Pro Thr Thr Ile Lys Val Gln Lys Lys Ala Gly Thr Pro
        35                  40                  45

Gly Arg Ser Ile Asp Val Phe Ala Val Gln Cys Glu Lys Cys Met Lys
    50                  55                  60

Trp Arg Lys Ile Asp Thr Gln Asp Glu Tyr Glu Asp Ile Arg Ser Arg
65                  70                  75                  80

Val Gln Glu Asp Pro Phe Phe Cys Lys Thr Lys Glu Gly Val Ser Cys
                85                  90                  95
```

-continued

Glu Asp Val Gly Asp Leu Asn Tyr Asp Ser Ser Arg Thr Trp Val Ile
            100                 105                 110

Asp Lys Pro Gly Leu Pro Arg Thr Pro Arg Gly Phe Lys Arg Ser Leu
        115                 120                 125

Ile Leu Arg Lys Asp Tyr Ser Lys Met Asp Ala Tyr Tyr Ile Thr Pro
    130                 135                 140

Thr Gly Lys Lys Leu Lys Ser Arg Asn Glu Ile Ala Ala Phe Ile Asp
145                 150                 155                 160

Ala Asn Gln Asp Tyr Lys Tyr Ala Leu Leu Gly Asp Phe Asn Phe Thr
                165                 170                 175

Val Pro Lys Val Met Glu Thr Val Pro Ser Gly Ile Leu Ser Asp
            180                 185                 190

Arg Thr Pro Lys Pro Ser Arg Lys Val Thr Ile Asp
        195                 200

<210> SEQ ID NO 10
<211> LENGTH: 804
<212> TYPE: PRT
<213> ORGANISM: Arabidopsis thaliana
<220> FEATURE:
<221> NAME/KEY: MISC_FEATURE
<222> LOCATION: (1)..(804)
<223> OTHER INFORMATION: Ceres GEMINI ID 5110C8
<220> FEATURE:
<221> NAME/KEY: MISC_FEATURE
<222> LOCATION: (1)..(804)
<223> OTHER INFORMATION: Ceres CDNA ID no. 23655935

<400> SEQUENCE: 10

Met Ser Gly Ser Leu Gly Leu Thr Pro Ala Ser Leu Lys Ala Ser Gly
1               5                   10                  15

Arg Ser Ser Glu Asn Val Ser Leu Leu Thr Leu Gln Gly Lys Ile Lys
            20                  25                  30

Arg Asp Pro Glu Gly Tyr Glu Thr Glu Leu Gln Leu Ile Tyr Lys Gln
        35                  40                  45

Phe Lys Thr Ser Val Asp Leu Phe His Glu Leu Ala Ala Leu Ser Phe
    50                  55                  60

Ser Ser Thr Gly Gly Ile Gly Ser Asp Pro Ser Val Ser Lys Asp Leu
65                  70                  75                  80

Gly Asp Arg Ala Met Phe Leu Ala His Val Thr Pro Phe Tyr Pro Lys
                85                  90                  95

Gln Leu Ala Ala Phe Pro Ala Gln Leu Thr Gly Leu Leu Arg Thr Ser
            100                 105                 110

Cys Leu Ala Met Pro Ser Gly Leu Arg Asn His Ile Ala Gln Ala Leu
        115                 120                 125

Ile Leu Leu Met Asn Arg Lys Ser Leu Val Ile Glu Asp Leu Leu Ala
    130                 135                 140

Leu Phe Leu Asp Ile Gln Thr Leu Gly Asp Lys Asn Leu Arg Asn Leu
145                 150                 155                 160

Ala Phe Gly His Ile Val Gln Thr Ile Arg Lys Met Ser Ile Thr Asp
                165                 170                 175

Pro Lys His Lys Ser Leu Gln Lys Ile Val Ser Met Leu Glu Gln
            180                 185                 190

Glu Asp Glu Ala Lys Ala Lys Arg Ala Leu Ala Thr Leu Cys Ala Leu
        195                 200                 205

His Lys Lys Lys Ile Trp Leu Gly Asp Lys Asn Glu Arg Val Ala Ile
    210                 215                 220

-continued

```
Ala Ile Cys Glu Ala Cys Phe His Ser Ser Pro Arg Ile Met Ile Ser
225                 230                 235                 240

Ala Leu Arg Phe Leu Leu Asp Tyr Glu Asn Ile Asp Asp Asp Asp Asp
            245                 250                 255

Ser Asp Ala Glu Ser Asp Asp Glu Glu Ser Lys Lys Ile Asp Gln
        260                 265                 270

Val Val Ile Asn Arg Gln Ala Val Tyr Lys Ala Asn Asn Lys Gly Thr
            275                 280                 285

Ser Ser Ser Lys Lys Lys Lys Gln Ala Lys Leu Gln Arg Ala Val Lys
    290                 295                 300

Ser Ile Lys Arg Lys Gln Arg Ser Ser Ser Glu Asn Thr Thr Ser Thr
305                 310                 315                 320

Phe Ser Pro Leu Asn His Leu Asn Asp Ala Gln Lys Phe Ala Glu Lys
                325                 330                 335

Leu Phe Ser Arg Leu Gln Thr Ile Lys Gly Ser Gly Glu Arg Val Glu
            340                 345                 350

Thr Arg Leu Met Met Ile Lys Val Ile Ala Arg Thr Ile Gly Leu His
            355                 360                 365

Lys Leu His Leu Leu Ser Phe Tyr Pro Phe Leu Gln Asn Tyr Ala Leu
370                 375                 380

Pro His Val Lys Asp Ile Thr Gln Ile Leu Ala Ala Val Gln Ser
385                 390                 395                 400

Cys His Asp Gly Val Pro Ser Asp Val Val Glu Pro Leu Phe Lys Gln
                405                 410                 415

Ile Val Asn Gln Phe Val His Asp Lys Ser Arg Pro Glu Ala Ile Ala
            420                 425                 430

Val Gly Leu Asn Val Val Arg Glu Met Cys Leu Arg Val His Asp Leu
        435                 440                 445

Met Thr Glu Glu Leu Leu Gln Asp Leu Ala Leu Tyr Lys Lys Ser His
    450                 455                 460

Glu Lys Ala Ile Ser Ala Ala Ala Arg Ser Leu Ile Ala Leu Phe Arg
465                 470                 475                 480

Glu Ile Asn Pro Ser Leu Leu Val Lys Lys Asp Arg Gly Arg Pro Gly
                485                 490                 495

Ala Thr Val Phe Ile Pro Lys His Tyr Gly Glu Ser Asn Val Phe Ser
            500                 505                 510

Asn Val Pro Asn Val Glu Leu Leu Gln Glu Ser Asp Asn Glu Ser Gly
        515                 520                 525

Ser Asp Gly Asp Gln Asp Asp Gly Val Glu Leu Pro Ile Gly Asp
    530                 535                 540

Asp Val Glu Gln Glu Leu Ile Pro Gly Asp Cys Gly Ser Glu Asp Lys
545                 550                 555                 560

Ala Glu Glu Asp Ser Asn Asp Gly Asp Met Asn Asn Thr Glu Asp
                565                 570                 575

Asp Ser Asp Ile Asp Thr Ser Ile Gly Gly Asp Glu Asp Glu Glu Val
            580                 585                 590

Asn Asp Ser Asp Glu Ala Asp Thr Asp Ser Glu Asn Glu Glu Ile Glu
        595                 600                 605

Ser Glu Glu Glu Asp Gly Glu Ala Ser Asp Ser Ser Val Glu Asp Ser
    610                 615                 620

Gly Asn Lys Glu Lys Ala Lys Gly Lys Lys Arg Lys Ile Val Asp Phe
625                 630                 635                 640
```

-continued

```
Asp Ala Asn Leu Leu Ser Ala Asp Thr Ser Leu Arg Ala Leu Lys Arg
                645                 650                 655

Phe Ala Glu Ala Lys Asn Glu Lys Pro Ser Phe Asp Glu Gly Asp Gly
            660                 665                 670

Ile Leu Ser Asn Glu Asp Phe Arg Lys Ile Lys Thr Leu Gln Ala Lys
        675                 680                 685

Lys Glu Ala Lys Ile Ala Leu Ala Arg Lys Gly Phe Lys Val Pro Asn
    690                 695                 700

Ser Asp Gln Leu Ser Lys Lys Arg Val Asp Pro Ala Lys Leu Glu Ala
705                 710                 715                 720

His Ile Arg His Lys Leu Thr Lys Glu Gln Arg Leu Glu Leu Val Lys
                725                 730                 735

Ala Gly Arg Glu Asp Arg Gly Lys Tyr Lys Ser Lys Ala Ala Val Lys
            740                 745                 750

Gln Lys Lys Thr Gly Gly Ser Ser Asn Lys Gln Lys Glu His Arg Lys
        755                 760                 765

Asn Met Pro Leu Ala Ala Ile Arg Ser Lys Ala Gly Lys Ser Lys Arg
    770                 775                 780

Ile Lys Lys Met Lys Asn Ser Ile Ser Gly Ser Gln Phe Arg Gly Arg
785                 790                 795                 800

Lys Ala Trp Lys

<210> SEQ ID NO 11
<211> LENGTH: 343
<212> TYPE: PRT
<213> ORGANISM: Arabidopsis thaliana
<220> FEATURE:
<221> NAME/KEY: MISC_FEATURE
<222> LOCATION: (1)..(343)
<223> OTHER INFORMATION: Ceres GEMINI ID 555A1
<220> FEATURE:
<221> NAME/KEY: MISC_FEATURE
<222> LOCATION: (1)..(343)
<223> OTHER INFORMATION: Ceres CLONE ID 117089
<220> FEATURE:
<221> NAME/KEY: MISC_FEATURE
<222> LOCATION: (1)..(343)
<223> OTHER INFORMATION: cDNA ID no. 23388445

<400> SEQUENCE: 11

Met Ser Asp Ser Gly Glu Pro Lys Pro Ser Gln Gln Glu Glu Pro Leu
1               5                   10                  15

Pro Gln Pro Ala Ala Gln Glu Thr Gln Ser Gln Gln Val Cys Thr Phe
            20                  25                  30

Phe Lys Lys Pro Thr Lys Ser Lys Asn Ile Arg Lys Arg Thr Ile Asp
        35                  40                  45

Ala Asp Glu Glu Asp Gly Asp Ser Lys Ser Glu Ser Ser Ile Leu Gln
    50                  55                  60

Asn Leu Lys Lys Val Ala Lys Pro Asp Ser Lys Leu Tyr Phe Ser Ser
65                  70                  75                  80

Gly Pro Ser Lys Ser Ser Thr Thr Thr Ser Gly Ala Pro Glu Arg Ser
                85                  90                  95

Val Phe His Tyr Asp Ser Ser Lys Glu Ile Gln Val Gln Asn Asp Ser
            100                 105                 110

Gly Ala Thr Ala Thr Leu Glu Thr Glu Thr Asp Phe Asn Gln Asp Ala
        115                 120                 125

Arg Ala Ile Arg Glu Arg Val Leu Lys Lys Ala Asp Glu Ala Leu Lys
    130                 135                 140
```

```
Gly Asn Lys Lys Lys Ala Ser Asp Glu Lys Leu Tyr Lys Gly Ile His
145                 150                 155                 160

Gly Tyr Thr Asp His Lys Ala Gly Phe Arg Arg Glu Gln Thr Ile Ser
                165                 170                 175

Ser Glu Lys Ala Gly Gly Ser His Gly Pro Leu Arg Ala Ser Ala His
            180                 185                 190

Ile Arg Val Ser Ala Arg Phe Asp Tyr Gln Pro Asp Ile Cys Lys Asp
        195                 200                 205

Tyr Lys Glu Thr Gly Tyr Cys Gly Tyr Gly Asp Ser Cys Lys Phe Leu
    210                 215                 220

His Asp Arg Gly Asp Tyr Lys Pro Gly Trp Gln Ile Glu Lys Glu Trp
225                 230                 235                 240

Glu Glu Ala Glu Lys Val Arg Lys Arg Asn Lys Ala Met Gly Val Glu
                245                 250                 255

Asp Glu Asp Asp Glu Ala Asp Lys Asp Ser Asp Glu Asp Glu Asn Ala
            260                 265                 270

Leu Pro Phe Ala Cys Phe Ile Cys Arg Glu Pro Phe Val Asp Pro Val
        275                 280                 285

Val Thr Lys Cys Lys His Tyr Phe Cys Glu His Cys Ala Leu Lys His
    290                 295                 300

His Thr Lys Asn Lys Lys Cys Phe Val Cys Asn Gln Pro Thr Met Gly
305                 310                 315                 320

Ile Phe Asn Ala Ala His Glu Ile Lys Lys Arg Met Ala Glu Glu Arg
                325                 330                 335

Ser Lys Ala Glu Glu Gly Leu
            340

<210> SEQ ID NO 12
<211> LENGTH: 84
<212> TYPE: PRT
<213> ORGANISM: Zea mays
<220> FEATURE:
<221> NAME/KEY: MISC_FEATURE
<222> LOCATION: (1)..(84)
<223> OTHER INFORMATION: Ceres GEMINI ID 552G1
<220> FEATURE:
<221> NAME/KEY: MISC_FEATURE
<222> LOCATION: (1)..(84)
<223> OTHER INFORMATION: Ceres CLONE ID 304947
<220> FEATURE:
<221> NAME/KEY: MISC_FEATURE
<222> LOCATION: (1)..(84)
<223> OTHER INFORMATION: Ceres CDNA ID no. 23777863

<400> SEQUENCE: 12

Met Leu Pro Ala Glu Phe Glu Ile Thr Asp Cys Cys His Pro Cys Asp
1               5                   10                  15

Ser Asp Lys Glu Asn Val Leu Ala Ile Gln Val Met Arg Trp Ser Asp
            20                  25                  30

Gly Ser Tyr Leu Glu Asp Gln Asp His Trp Arg Leu Ser Gly Ser Leu
        35                  40                  45

Ser Asp Asn Phe Phe Ala Ile Ile Val Pro Thr Glu Tyr Asp Cys Leu
    50                  55                  60

Thr Ala Ser Thr Arg Lys Lys Glu Ile Val Asp Val Ile Val Lys Ala
65                  70                  75                  80

Phe Lys Ser Thr

<210> SEQ ID NO 13
<211> LENGTH: 344
```

```
<212> TYPE: PRT
<213> ORGANISM: Arabidopsis thaliana
<220> FEATURE:
<221> NAME/KEY: MISC_FEATURE
<222> LOCATION: (1)..(344)
<223> OTHER INFORMATION: Ceres GEMINI ID 555A3
<220> FEATURE:
<221> NAME/KEY: MISC_FEATURE
<222> LOCATION: (1)..(344)
<223> OTHER INFORMATION: Ceres CLONE ID 1959
<220> FEATURE:
<221> NAME/KEY: MISC_FEATURE
<222> LOCATION: (1)..(344)
<223> OTHER INFORMATION: Ceres CDNA ID no. 23377122

<400> SEQUENCE: 13
```

Met Met Met Phe Lys Ser Gly Asp Met Asp Tyr Thr Gln Lys Met Lys
1               5                   10                  15

Arg Cys His Glu Tyr Val Glu Ala Leu Glu Glu Gln Lys Lys Ile
            20                  25                  30

Gln Val Phe Gln Arg Glu Leu Pro Leu Cys Leu Glu Val Thr Gln
        35                  40                  45

Ala Ile Glu Ser Cys Arg Lys Glu Leu Ser Ser Ser Glu His Val
50                  55                  60

Gly Gly Gln Ser Glu Cys Ser Glu Arg Thr Thr Ser Glu Cys Gly Gly
65                  70                  75                  80

Ala Val Phe Glu Glu Phe Met Pro Ile Lys Trp Ser Ala Ser Ser
                85                  90                  95

Asp Glu Thr Asp Lys Asp Glu Glu Ala Glu Lys Thr Glu Met Met Thr
                100                 105                 110

Asn Glu Asn Asn Asp Gly Asp Lys Lys Lys Ser Asp Trp Leu Arg Ser
            115                 120                 125

Val Gln Leu Trp Asn Gln Ser Pro Asp Pro Gln Pro Asn Asn Lys Lys
130                 135                 140

Pro Met Val Ile Glu Val Lys Arg Ser Ala Gly Ala Phe Gln Pro Phe
145                 150                 155                 160

Gln Lys Glu Lys Pro Lys Ala Ala Asp Ser Gln Pro Leu Ile Lys Ala
                165                 170                 175

Ile Thr Pro Thr Ser Thr Thr Thr Ser Ser Thr Ala Glu Thr Val
            180                 185                 190

Gly Gly Gly Lys Glu Phe Glu Glu Gln Lys Gln Ser His Ser Asn Arg
            195                 200                 205

Lys Gln Arg Arg Cys Trp Ser Pro Glu Leu His Arg Arg Phe Leu His
        210                 215                 220

Ala Leu Gln Gln Leu Gly Gly Ser His Val Ala Thr Pro Lys Gln Ile
225                 230                 235                 240

Arg Asp Leu Met Lys Val Asp Gly Leu Thr Asn Asp Glu Val Lys Ser
                245                 250                 255

His Leu Gln Lys Tyr Arg Leu His Thr Arg Arg Pro Ala Thr Pro Val
            260                 265                 270

Val Arg Thr Gly Gly Glu Asn Pro Gln Gln Arg Gln Phe Met Val Met
        275                 280                 285

Glu Gly Ile Trp Val Pro Ser His Asp Thr Thr Asn Asn Arg Val Tyr
290                 295                 300

Ala Pro Val Ala Ser Gln Pro Pro Gln Ser Ser Thr Ser Gly Glu Arg
305                 310                 315                 320

Ser Asn Arg Gly Cys Lys Ser Pro Ala Thr Ser Ser Thr Thr His
            325                 330                 335

Thr Pro His Leu Leu Pro Leu Ser
        340

<210> SEQ ID NO 14
<211> LENGTH: 349
<212> TYPE: PRT
<213> ORGANISM: Glycine max
<220> FEATURE:
<221> NAME/KEY: MISC_FEATURE
<222> LOCATION: (1)..(349)
<223> OTHER INFORMATION: Ceres GEMINI ID 555C4
<220> FEATURE:
<221> NAME/KEY: MISC_FEATURE
<222> LOCATION: (1)..(349)
<223> OTHER INFORMATION: Ceres CLONE ID 674157
<220> FEATURE:
<221> NAME/KEY: MISC_FEATURE
<222> LOCATION: (1)..(349)
<223> OTHER INFORMATION: cDNA ID no. 23704869

<400> SEQUENCE: 14

Met Ile Ser Pro Asn Pro Pro Leu Arg Leu Arg His Thr Ala Ala Phe
1               5                   10                  15

Cys Pro Val Thr Leu Val Pro Trp Pro Leu Thr Pro Arg Asn Thr Arg
            20                  25                  30

Pro Phe Ser Arg Ala Ser Ser Thr Xaa Ala Cys Ala Ala Val Ala Met
        35                  40                  45

Thr Arg Gly Ser Leu Ala Lys Ser Gln Asp Pro Ser Pro Phe Ser Asp
    50                  55                  60

Gly Gly Ser Gln Pro Thr Asn Pro Ser Leu Val Gly Ser Gln Thr Thr
65                  70                  75                  80

Ser Lys Gly Ser Ile Pro Ser Gly Asn Asp Gln Ser Lys Leu Gln Asp
                85                  90                  95

Lys Asp Ile Asn Ala Pro Val Gly Ile Pro Ser Ile Pro Ala Ile Gln
            100                 105                 110

Lys Lys Pro Ala Val Ala Ile Arg Pro Ser Thr Ser Gly Ser Ser Arg
        115                 120                 125

Glu Gln Ser Asp Asp Glu Asp Ile Glu Gly Glu Thr Ser Met Asn Asp
    130                 135                 140

Asn Thr Asp Pro Ala Asp Val Lys Arg Val Arg Arg Met Leu Ser Asn
145                 150                 155                 160

Arg Glu Ser Ala Arg Arg Ser Arg Arg Lys Gln Ala His Leu Thr
                165                 170                 175

Asp Leu Glu Thr Gln Val Ser Gln Leu Arg Gly Glu Asn Ser Thr Leu
            180                 185                 190

Leu Lys Arg Leu Thr Asp Val Ser Gln Lys Tyr Ser Asp Ser Ala Val
        195                 200                 205

Asp Asn Arg Val Leu Lys Ala Asp Val Glu Thr Leu Arg Ala Lys Val
    210                 215                 220

Lys Met Ala Glu Glu Thr Val Lys Arg Ile Thr Gly Leu Asn Pro Met
225                 230                 235                 240

Pro His Ala Met Ser Asp Ile Ser Ser Leu Gly Leu Pro Ser Phe Asp
                245                 250                 255

Gly Arg Ser Pro Ser Asp Thr Ser Ala Asp Ala Ser Val Pro Val Gln
            260                 265                 270

Asp Asp Pro His His His Phe Tyr Gln Pro Thr Leu Asn Asn Pro Ile
        275                 280                 285

Pro Ser His Asp Pro Ile Val Asn Asn Gly Leu Gly Gly Ile Ser Ser

```
            290                 295                 300
Ile Glu Asn Val Gln Gln Gln Asn Ala Ala Ala Val Val Gly Gly Asn
305                 310                 315                 320

Lys Ile Gly Gln Thr Ala Ser Leu Gln Arg Val Ala Ser Leu Glu His
                325                 330                 335

Leu Gln Lys Arg Ile Arg Gly Gly Pro Pro Ser Glu Gln
            340                 345

<210> SEQ ID NO 15
<211> LENGTH: 463
<212> TYPE: PRT
<213> ORGANISM: Arabidopsis thaliana
<220> FEATURE:
<221> NAME/KEY: MISC_FEATURE
<222> LOCATION: (1)..(463)
<223> OTHER INFORMATION: Zap1
<220> FEATURE:
<221> NAME/KEY: MISC_FEATURE
<222> LOCATION: (1)..(463)
<223> OTHER INFORMATION: Ceres cDNA ID no. 23468313

<400> SEQUENCE: 15

Met Ala Glu Val Gly Lys Val Leu Ala Ser Asp Met Glu Leu Asp His
1               5                   10                  15

Ser Asn Glu Thr Lys Ala Val Asp Asp Val Val Ala Thr Thr Asp Lys
            20                  25                  30

Ala Glu Val Ile Pro Val Ala Val Thr Arg Thr Glu Thr Val Val Glu
        35                  40                  45

Ser Leu Glu Ser Thr Asp Cys Lys Glu Leu Glu Lys Leu Val Pro His
    50                  55                  60

Thr Val Ala Ser Gln Ser Glu Val Asp Val Ala Ser Pro Val Ser Glu
65                  70                  75                  80

Lys Ala Pro Lys Val Ser Glu Ser Ser Gly Ala Leu Ser Leu Gln Ser
                85                  90                  95

Gly Ser Glu Gly Asn Ser Pro Phe Ile Arg Glu Lys Val Met Glu Asp
            100                 105                 110

Gly Tyr Asn Trp Arg Lys Tyr Gly Gln Lys Leu Val Lys Gly Asn Glu
        115                 120                 125

Phe Val Arg Ser Tyr Tyr Arg Cys Thr His Pro Asn Cys Lys Ala Lys
130                 135                 140

Lys Gln Leu Glu Arg Ser Ala Gly Gly Gln Val Val Asp Thr Val Tyr
145                 150                 155                 160

Phe Gly Glu His Asp His Pro Lys Pro Leu Ala Gly Ala Val Pro Ile
                165                 170                 175

Asn Gln Asp Lys Arg Ser Asp Val Phe Thr Ala Val Ser Lys Glu Lys
            180                 185                 190

Thr Ser Gly Ser Ser Val Gln Thr Leu Arg Gln Thr Glu Pro Pro Lys
        195                 200                 205

Ile His Gly Gly Leu His Val Ser Val Ile Pro Pro Ala Asp Asp Val
    210                 215                 220

Lys Thr Asp Ile Ser Gln Ser Ser Arg Ile Thr Gly Asp Asn Thr His
225                 230                 235                 240

Lys Asp Tyr Asn Ser Pro Thr Ala Lys Arg Lys Lys Gly Gly Asn
                245                 250                 255

Ile Glu Leu Ser Pro Val Glu Arg Ser Thr Asn Asp Ser Arg Ile Val
            260                 265                 270

Val His Thr Gln Thr Leu Phe Asp Ile Val Asn Asp Gly Tyr Arg Trp
```

-continued

```
                275                 280                 285
Arg Lys Tyr Gly Gln Lys Ser Val Lys Gly Ser Pro Tyr Pro Arg Ser
        290                 295                 300

Tyr Tyr Arg Cys Ser Ser Pro Gly Cys Pro Val Lys Lys His Val Glu
305                 310                 315                 320

Arg Ser Ser His Asp Thr Lys Leu Leu Ile Thr Thr Tyr Glu Gly Lys
                325                 330                 335

His Asp His Asp Met Pro Pro Gly Arg Val Val Thr His Asn Asn Met
        340                 345                 350

Leu Asp Ser Glu Val Asp Asp Lys Gly Asp Ala Asn Lys Thr Pro
        355                 360                 365

Gln Ser Ser Thr Leu Gln Ser Ile Thr Lys Asp Gln His Val Glu Asp
370                 375                 380

His Leu Arg Lys Lys Thr Lys Thr Asn Gly Phe Glu Lys Ser Leu Asp
385                 390                 395                 400

Gln Gly Pro Val Leu Asp Glu Lys Leu Lys Glu Ile Lys Glu Arg
                405                 410                 415

Ser Asp Ala Asn Lys Asp His Ala Ala Asn His Ala Lys Pro Glu Ala
        420                 425                 430

Lys Ser Asp Asp Lys Thr Thr Val Cys Gln Glu Lys Ala Val Gly Thr
        435                 440                 445

Leu Glu Ser Glu Glu Gln Lys Pro Lys Thr Glu Pro Ala Gln Ser
        450                 455                 460

<210> SEQ ID NO 16
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: Ps-CR-PR3

<400> SEQUENCE: 16
ctgtatcgaa gtgtctataa cccacctct                                  29

<210> SEQ ID NO 17
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(26)
<223> OTHER INFORMATION: Ps-CR-PR2

<400> SEQUENCE: 17
ccaatttcac tctttcagac ccttga                                     26

<210> SEQ ID NO 18
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Ps-CR-PR1
```

```
<400> SEQUENCE: 18
caggtacacc accgatctcc attct                                              25

<210> SEQ ID NO 19
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(16)
<223> OTHER INFORMATION: AD2
<220> FEATURE:
<221> NAME/KEY: misc_feature
<222> LOCATION: (1)..(1)
<223> OTHER INFORMATION: n is a, c, t, g, unknown, or other
<220> FEATURE:
<221> NAME/KEY: misc_feature
<222> LOCATION: (11)..(11)
<223> OTHER INFORMATION: n is a, c, t, g, unknown, or other

<400> SEQUENCE: 19
ngtcgaswga nawgaa                                                        16

<210> SEQ ID NO 20
<211> LENGTH: 52
<212> TYPE: DNA
<213> ORGANISM: Artificial Sequence
<220> FEATURE:
<223> OTHER INFORMATION: Linker/Adaptor top strand

<400> SEQUENCE: 20
ggcccgggct gcgatcatca aggaagtaag cgtggtcgac ggcccgggct gc                52

<210> SEQ ID NO 21
<211> LENGTH: 25
<212> TYPE: DNA
<213> ORGANISM: Artificial Sequence
<220> FEATURE:
<223> OTHER INFORMATION: Linker/Adaptor bottom strand
<220> FEATURE:
<221> NAME/KEY: misc_feature
<222> LOCATION: (1)..(1)
<223> OTHER INFORMATION: modified with the addition of a phosphate group
<220> FEATURE:
<221> NAME/KEY: misc_feature
<222> LOCATION: (25)..(25)
<223> OTHER INFORMATION: modified with the addition of an amino group

<400> SEQUENCE: 21
ctaggcagcc cgggccgtcg accac                                              25

<210> SEQ ID NO 22
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(17)
<223> OTHER INFORMATION: YES3-5

<400> SEQUENCE: 22
gatcatcaag gaagtaa                                                       17

<210> SEQ ID NO 23
<211> LENGTH: 22
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(22)
<223> OTHER INFORMATION: Ec-NMCH3-PR1

<400> SEQUENCE: 23
gaggaggatg ggcttctcca ta                                    22

<210> SEQ ID NO 24
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: NAP2

<400> SEQUENCE: 24
tcgacggccc gggctgccta g                                     21

<210> SEQ ID NO 25
<211> LENGTH: 26
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(26)
<223> OTHER INFORMATION: Ec-NMCH3-PR2

<400> SEQUENCE: 25
agctacctga tattcttggg aggaga                                26

<210> SEQ ID NO 26
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(16)
<223> OTHER INFORMATION: M13-F

<400> SEQUENCE: 26
gtaaaacgac ggccag                                           16

<210> SEQ ID NO 27
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(17)
<223> OTHER INFORMATION: M13-R

<400> SEQUENCE: 27
caggaaacag ctatgac                                          17

<210> SEQ ID NO 28
```

```
<211> LENGTH: 21
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(21)
<223> OTHER INFORMATION: Ps-ROMT-PR3

<400> SEQUENCE: 28
ccattgaatc cacgaatgcg a                                              21

<210> SEQ ID NO 29
<211> LENGTH: 24
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(24)
<223> OTHER INFORMATION: Ps-ROMT-PR2

<400> SEQUENCE: 29
gcttgccctt tcaacctttc ttct                                           24

<210> SEQ ID NO 30
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Ps-SAT-PR3

<400> SEQUENCE: 30
ggagttgtgg gtttaatggt ttcct                                          25

<210> SEQ ID NO 31
<211> LENGTH: 29
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(29)
<223> OTHER INFORMATION: Ps-SAT-PR2

<400> SEQUENCE: 31
atcacttcaa cagcagcact atacattgt                                      29

<210> SEQ ID NO 32
<211> LENGTH: 25
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(25)
<223> OTHER INFORMATION: Ps-HMCOMT2-PR3

<400> SEQUENCE: 32
gatggaaact tcttgtgttg cagca                                          25
```

```
<210> SEQ ID NO 33
<211> LENGTH: 28
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (1)..(28)
<223> OTHER INFORMATION: Ps-HMCOMT2-PR2

<400> SEQUENCE: 33
gcatctaaac tacccattag atatgcga                                          28

<210> SEQ ID NO 34
<211> LENGTH: 290
<212> TYPE: PRT
<213> ORGANISM: Arabidopsis thaliana
<220> FEATURE:
<221> NAME/KEY: MISC_FEATURE
<222> LOCATION: (1)..(290)
<223> OTHER INFORMATION: Ceres GEMINI ID 5110C9
<220> FEATURE:
<221> NAME/KEY: MISC_FEATURE
<222> LOCATION: (1)..(290)
<223> OTHER INFORMATION: Ceres CDNA ID no. 23660631

<400> SEQUENCE: 34
```

Met Ala Met Ala Ser Ala Ser Gly Ser Ala Leu Cys Phe Thr Asp Ala
1               5                   10                  15

Ser Ser Ser Leu Ala Leu Arg Arg Asp Cys Gly Ala Leu Cys Leu Pro
            20                  25                  30

Pro Arg Thr Val Thr Phe Gly Phe Val Asp Lys Pro Leu Val Asn Leu
        35                  40                  45

Glu Arg Leu Arg Leu Ser Thr Leu Lys Ile Arg Ala Ser Asn Ala Thr
    50                  55                  60

Ala Val Glu Asn Gly Lys Gln Glu Gly Ser Ala Ala Asp Ser Asp Lys
65                  70                  75                  80

Val Pro Thr Pro Val Val Ile Ile Asp Gln Asp Ser Asp Pro Asp Ala
                85                  90                  95

Thr Val Leu Glu Val Thr Phe Gly Asp Arg Leu Gly Ala Leu Leu Asp
            100                 105                 110

Thr Met Asn Ala Leu Lys Asn Leu Gly Leu Asn Val Val Lys Ala Asn
        115                 120                 125

Val Tyr Leu Asp Ser Ser Gly Lys His Asn Lys Phe Ala Ile Thr Arg
    130                 135                 140

Ala Asp Ser Gly Arg Lys Val Glu Asp Pro Glu Leu Leu Glu Ala Ile
145                 150                 155                 160

Arg Leu Thr Val Ile Asn Asn Leu Leu Glu Phe His Pro Glu Ser Ser
                165                 170                 175

Ser Gln Leu Ala Met Gly Ala Ala Phe Gly Val Leu Pro Pro Thr Glu
            180                 185                 190

Pro Ile Asp Val Asp Ile Ala Thr His Ile Thr Ile Glu Asp Asp Gly
        195                 200                 205

Pro Asp Arg Ser Leu Leu Phe Ile Glu Ser Ala Asp Arg Pro Gly Leu
    210                 215                 220

Leu Val Glu Leu Val Lys Ile Ile Ser Asp Ile Ser Val Ala Val Glu
225                 230                 235                 240

Ser Gly Glu Phe Asp Thr Glu Gly Leu Leu Ala Lys Val Lys Phe His
                245                 250                 255

```
-continued

Val Ser Tyr Arg Asn Lys Ala Leu Ile Lys Pro Leu Gln Gln Val Leu
            260                 265                 270

Ala Asn Ser Leu Arg Tyr Phe Leu Arg Arg Pro Ser Thr Asp Glu Ser
            275                 280                 285

Ser Phe
    290
```

REGULATORY REGIONS FROM PAPAVERACEAE

CROSS-REFERENCE TO RELATED APPLICATIONS

This application claims priority under 35 U.S.C. §119 to U.S. Provisional Application No. 60/673,307, filed Apr. 20, 2005, which is incorporated herein by reference in its entirety.

TECHNICAL FIELD

The present invention relates to compositions and methods involving regulatory regions from *Papaveraceae* species.

INCORPORATION-BY-REFERENCE & TEXT

The material on the accompanying diskette is hereby incorporated by reference into this application. The accompanying diskette contain one file, 60340963.txt, which was created on Feb. 21, 2006. The file named 60340963.txt is 43 KB. The file can be accessed using Microsoft Word on a computer that uses Windows OS.

BACKGROUND

An essential element for genetic engineering of plants is the ability to express genes using various regulatory regions. The expression pattern of a transgene, conferred by a regulatory region is critical for the timing, location, and conditions under which a transgene is expressed, as well as the intensity with which the transgene is expressed in a transgenic plant. There is continuing need for suitable regulatory regions that can facilitate transcription of sequences that are operably linked to the regulatory region.

SUMMARY

In one aspect, the invention features an isolated nucleic acid comprising a regulatory region having the nucleotide sequence of SEQ ID NOs:1, 2, 3, 4, 5, or 6. In some embodiments, the regulatory region has a nucleotide sequence complementary to SEQ ID NOs: 1, 2, 3, 4, 5, or 6. In some embodiments, the regulatory region is at least 300 nucleotides in length and has 70% or greater sequence identity to SEQ ID NOs: 1, 2, 3, 4, 5, or 6, e.g., at least 90%, 91%, 92%, 93%, 94%, 95%, 96%, 97%, 98%, or 99% sequence identity to SEQ ID NOs: 1, 2, 3, 4, 5, or 6. A nucleic acid construct can comprise such a regulatory region, operably linked to a heterologous nucleic acid. The heterologous nucleic acid can encode a polypeptide. A transgenic plant can comprise at least one such nucleic acid construct, e.g., first and second nucleic acid constructs, each construct having a regulatory region operably linked to a heterologous nucleic acid. In some cases, the regulatory region of the first nucleic acid construct is different from the regulatory region of the second nucleic acid construct. The plant can be a dicotyledonous plant or a monocotyledonous plant. In some embodiments, the heterologous nucleic acid is a coding sequence for a regulatory protein involved in alkaloid biosynthesis. In some embodiments, the heterologous nucleic acid is a coding sequence for an enzyme involved in alkaloid biosynthesis, e.g., salutaridinol 7-O-acetyltransferase, salutaridine synthase, salutaridine reductase, morphine 6-dehydrogenase; or codeinone reductase. In some embodiments, the heterologous nucleic acid is transcribed into an interfering RNA against a gene coding for a protein involved in alkaloid biosynthesis or an interfering RNA against a gene coding for a methylation status polypeptide.

In another aspect, the invention features a method for making a plant. The method comprises introducing into a plant at least one nucleic acid construct comprising a regulatory region having the nucleotide sequence of SEQ ID NOs: 1, 2, 3, 4, 5, or 6; a nucleotide sequence complementary to SEQ ID NOs: 1, 2, 3, 4, 5, or 6; or a sequence at least 300 nucleotides in length and having 70% or greater sequence identity to SEQ ID NOs: 1, 2, 3, 4, 5, or 6. The construct can comprise a heterologous nucleic acid operably linked to the regulatory region. In some embodiments, the heterologous nucleic acid encodes a regulatory protein involved in alkaloid biosynthesis. In some embodiments, the heterologous nucleic acid encodes an enzyme involved in alkaloid biosynthesis, e.g., salutaridinol 7-O-acetyltransferase, salutaridine synthase, salutaridine reductase, morphine 6-dehydrogenase; or codeinone reductase. In some embodiments, the heterologous nucleic acid is transcribed into an interfering RNA against a protein involved in alkaloid biosynthesis. The plant made by the method can be a monocotyledonous plant or a dicotyledonous plant such as a *Papaveraceae* plant.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1 is the nucleic acid sequence of a *Eschscholzia californica* N-methylcoclaurine 3'-hydroxylase (EcNMCH3) regulatory region.

FIG. 2 is the nucleic acid sequence of a *Papaver somniferum* (R,S)-reticuline 7-O-methyltransferase (PsROMT) regulatory region.

FIG. 3 is the nucleic acid sequence of a *Papaver somniferum* S-adenosyl-L-methionine:3'-hydroxy N-methylcoclaurine 4'-O-methyltransferase 2 (PsHMCOMT2) regulatory region.

FIG. 4 is the nucleic acid sequence of a *Papaver somniferum* salutaridinol 7-O-acetyltransferase (PsSAT) regulatory region.

FIG. 5 is the nucleic acid sequence of a *Papaver somniferum* PsCRX regulatory region.

FIG. 6 is the nucleic acid sequence of a *Papaver somniferum* PsCR3 regulatory region.

DETAILED DESCRIPTION

The present invention relates to the discovery of novel regulatory regions of alkaloid biosynthesis genes. These regions are useful for directing the transcription of sequences of interest in eukaryotic organisms.

Regulatory Regions

The present invention features isolated nucleic acids that comprise a regulatory region. A regulatory region described herein is a nucleic acid that regulates transcription of a heterologous nucleic acid, when the regulatory region is operably linked 5' to the heterologous nucleic acid. The terms "nucleic acid" and "polynucleotide" are used interchangeably herein, and refer to RNA or DNA, including cDNA, synthetic DNA or genomic DNA. A nucleic acid can be single- or double-stranded and, if single-stranded, can be either a coding or non-coding strand. An "isolated nucleic acid" lacks one or both of the nucleic acid sequences that flank the nucleic acid as it occurs in nature in the genome. Thus, an isolated nucleic acid includes, without limitation, a DNA molecule that exists as a separate molecule (e.g., a chemically synthesized nucleic acid, or a cDNA or genomic DNA fragment produced by PCR or by restriction endonuclease treatment) without flanking sequences. An isolated nucleic acid also refers to a DNA molecule that is incorporated into a vector, an autonomously replicating plasmid, a virus, or into the genomic DNA of a prokaryote or eukaryote. A nucleic acid existing among hundreds to millions of other nucleic acids within, for example, cDNA libraries, genomic libraries, or gel slices containing a genomic DNA restriction digest, is not an isolated nucleic acid.

The nucleic acid molecules depicted in FIGS. 1-6 are examples of regulatory regions disclosed herein. However, a regulatory region can have a nucleotide sequence that deviates from those shown in FIG. 1, 2, 3, 4, 5, or 6, while retaining the ability to regulate expression of an operably linked nucleic acid. For example, a regulatory region having 70% or greater (e.g., 80% or greater, 81% or greater, 82% or greater, 83% or greater, 84% or greater, 85% or greater, 86% or greater, 87% or greater, 88% or greater, 89% or greater, 90% or greater, 91% or greater, 92% or greater, 93% or greater, 94% or greater, 95% or greater, 96% or greater, 97% or greater, 98% or greater, or 99% or greater) sequence identity to any one of the nucleotide sequences depicted in SEQ ID NOs:1-6 can affect expression of an operably linked nucleic acid.

The term "percent sequence identity" refers to the degree of identity between any given query sequence, e.g., SEQ ID NO:1, and a subject sequence. A subject sequence typically has a length that is more than 80 percent, e.g., more than 82, 85, 87, 89, 90, 93, 95, 97, 99, 100, 105, 110, 115, or 120 percent, of the length of the query sequence. A percent identity for any subject nucleic acid relative to a query nucleic acid can be determined as follows. A query nucleic acid sequence is aligned to one or more subject nucleic acid sequences using the computer program ClustalW (version 1.83, default parameters), which allows alignments of nucleic acid sequences to be carried out across their entire length (global alignment). Chenna et al., *Nucleic Acids Res.*, 31(13):3497-500 (2003).

ClustalW calculates the best match between a query and one or more subject sequences, and aligns them so that identities, similarities and differences can be determined. Gaps of one or more residues can be inserted into a query sequence, a subject sequence, or both, to maximize sequence alignments. For fast pairwise alignment of nucleic acid sequences, the following parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: G, P, S, N, D, Q, E, R, K; residue-specific gap penalties: on. The ClustalW output is a sequence alignment that reflects the relationship between sequences. ClustalW can be run, for example, at the Baylor College of Medicine Search Launcher site (available on the World Wide Web at searchlauncher.bcm.tmc.edu/multi-align/multi-align) and at the European Bioinformatics Institute site (available on the World Wide Web at ebi.ac.uk/clustalw.

To determine a percent identity between a query sequence and a subject sequence, ClustalW divides the number of identities in the best alignment by the number of residues compared (gap positions are excluded), and multiplies the result by 100. The output is the percent identity of the subject sequence with respect to the query sequence. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2. It is also noted that the length value will always be an integer.

A regulatory region featured herein can be made by cloning 5' flanking sequences from a genomic alkaloid biosynthesis gene, as described in more detail below. Alternatively, a regulatory region can be made by chemical synthesis and/or polymerase chain reaction (PCR) technology. PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. PCR is described, for example in *PCR Primer: A Laboratory Manual*, Ed. by Dieffenbach, C. and Dveksler, G., Cold Spring Harbor Laboratory Press, 1995. Nucleic acids also can be amplified by ligase chain reaction, strand displacement amplification, self-sustained sequence replication or nucleic acid sequence-based amplification. See, for example, Lewis, Genetic Engineering News, 12(9):1 (1992); Guatelli et al., *Proc. Natl. Acad. Sci.* USA, 87:1874-1878 (1990); and Weiss, *Science*, 254:1292 (1991).

A fragment of a regulatory region described herein can be made by similar techniques. For example, fragments of a regulatory region can be made that contain nucleotides 1 to 250 of SEQ ID NO:1 or nucleotides 1 to 500 of SEQ ID NO:1. In another example, fragments of a regulatory region can include nucleotides 1 to 500 of SEQ ID NO:5 or nucleotides 100 to 700 of SEQ ID NO:5. Fragments of a regulatory region can be at least 100 nucleotides in length, e.g., about 200, 250, 300, or 350 nucleotides in length. The ability of fragments to affect expression of an operably linked nucleic acid can be assayed using methods known to one having ordinary skill in the art. In particular, a regulatory region fragment can be operably linked to a reporter nucleic acid and used to transiently or stably transform a cell, e.g., a plant cell. Suitable reporter nucleic acids include β-glucuronidase (GUS), green fluorescent protein (GFP) and luciferase (LUC). Expression of the gene product encoded by the reporter nucleic acid can be monitored in such transformed cells using standard techniques.

A regulatory region described herein or a fragment thereof can also be used as a hybridization probe or a PCR primer. Fragments of the regulatory regions disclosed herein can hybridize under high stringency conditions to the nucleotide sequences of SEQ ID NO:1, 2, 3, 4, 5, or 6, or fragments thereof. Hybridization typically involves Southern analysis (Southern blotting). See, for example, sections 9.37-9.52 of Sambrook et al., 1989, *"Molecular Cloning, A Laboratory Manual"*, second edition, Cold Spring Harbor Press, Plainview; N.Y. High stringency conditions involve the use of low ionic strength and high temperature for washing, for example, 0.015 M NaCl/0.0015 M sodium citrate (0.1× SSC), 0.1% sodium dodecyl sulfate (SDS) at 65° C. Alternatively, denaturing agents such as formamide can be employed during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is the use of 50% formamide, 5×SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 µg/mL), 0.1% SDS, and 10% dextran sulfate at 42° C., with washes at 42° C. in 0.2×SSC and 0.1% SDS.

A single stranded nucleic acid can also be made that is complementary to one strand of a regulatory region or fragment thereof.

Nucleic Acid Constructs

A nucleic acid construct includes a regulatory region as disclosed herein. A construct can also include a heterologous nucleic acid operably linked to the regulatory region, in which case the construct can be introduced into an organism and used to direct expression of the operably linked nucleic acid. As used herein, "heterologous nucleic acid" refers to a nucleic acid other than the naturally occurring coding sequence to which the regulatory region was operably linked in a plant. The heterologous nucleic acid can be operably linked to the regulatory region in sense or antisense orientation. "Operably linked" refers to covalent linkage of two nucleic acids such that transcription and, if the heterologous nucleic acid is a coding sequence in sense orientation, translation can occur.

In some embodiments, a heterologous nucleic acid is transcribed and translated into a polypeptide. Suitable polypeptides include, without limitation, polypeptides that affect growth, hormone production, photosynthetic efficiency, nutritional value, and oil or protein composition. Polypeptides also can provide, without limitation, resistance to environmental stresses such as drought and cold, pathogens, insects, or herbicides. For example, *Bacillus thuringiensis* toxin genes can be expressed in plants to provide insect resistance. See, for example, U.S. Pat. No. 5,380,831. Suitable polypeptides also include screenable and selectable markers such as green fluorescent protein, luciferase, β-glucuronidase, or neomycin phosphotransferase II. In some embodiments a heterologous nucleic acid encodes a polypeptide that confers nutrient transporter function, enhanced nutrient utilization, or female sterility.

In some cases, a heterologous nucleic acid is transcribed and translated into a polypeptide associated with alkaloid biosynthesis, such as an enzyme involved in biosynthesis of alkaloid compounds or a regulatory protein such as a transcription factor involved in biosynthesis of alkaloid compounds. Examples of enzymes involved in tetrahydrobenzylisoquinoline alkaloid biosynthesis include those coding for tyrosine decarboxylase (YDC or TYD; EC 4.1.1.25), norcoclaurine synthase (EC 4.2.1.78), coclaurine N-methyltransferase (EC 2.1.1.140), (R,S)-norcoclaurine 6-O-methyl transferase (NOMT; EC 2.1.1.128), S-adenosyl-L-methionine:3'-hydroxy-N-methylcoclaurine 4'-O-methyltransferase 1 (HMCOMT1; EC 2.1.1.116); S-adenosyl-L-methionine:3'-hydroxy-N-methylcoclaurine4'-O-methyltransferase 2 (HMCOMT2; EC 2.1.1.116); monophenol monooxygenase (EC 1.14.18.1), N-methylcoclaurine 3'-hydroxylase (NMCH; EC 1.14.13.71), (R,S)-reticuline 7-O-methyltransferase (ROMT); berbamunine synthase (EC 1.14.21.3), columbamine O-methyltransferase (EC 2.1.1.118), berberine bridge enzyme (BBE; EC 1.21.3.3), reticuline oxidase (EC 1.21.3.4), dehydro reticulinium ion reductase (EC 1.5.1.27), (R,S)-1-benzyl-1,2,3,4-tetrahydroisoquinoline N-methyltransferase (EC 2.1.1.115), (S)-scoulerine oxidase (EC 1.14.21.2), (S)-cheilanthifoline oxidase (EC 1.14.21.1), (S)-tetrahydroprotoberberine N-methyltransferase (EC 2.1.1.122), (S)-canadine synthase (EC 1.14.21.5), tetrahydroberberine oxidase (EC 1.3.3.8), columbamine oxidase (EC 1.21.3.2), and other enzymes, such as protopine-6-monooxygenase, related to the biosynthesis of tetrahydrobenzylisoquinoline alkaloids.

In some cases, a heterologous nucleic acid encodes an enzyme involved in benzophenanthridine alkaloid biosynthesis, e.g., those encoding dihydrobenzophenanthridine oxidase (EC 1.5.3.12), dihydrosanguinarine 10-hydroxylase (EC 1.14.13.56), 10-hydroxy-dihydrosanguinarine 10-O-methyltransferase (EC 2.1.1.119), dihydrochelirubine 12-hydroxylase (EC 1.14.13.57), 12-hydroxy-dihydrochelirubine 12-O-methyltransferase (EC 2.1.1.120), and other enzymes, including dihydrobenzophenanthridine oxidase and dihydrosanguinarine 10-monooxygenase.

In some cases, a heterologous nucleic acid encodes an enzyme involved in morphinan alkaloid biosynthesis, e.g., salutaridinol 7-O-acetyltransferase (SAT; EC 2.3.1.150), salutaridine synthase (EC 1.14.21.4), salutaridine reductase (EC 1.1.1.248), morphine 6-dehydrogenase (EC 1.1.1.218); and codeinone reductase (CR; EC 1.1.1.247).

In some embodiments, a heterologous nucleic acid encodes an enzyme involved in purine alkaloid biosynthesis such as xanthosine methyltransferase, 7-N-methylxanthine methyltransferase (theobromine synthase), or 3,7-dimethylxanthine methyltransferase (caffeine synthase). In some embodiments, a heterologous nucleic acid encodes an enzyme involved in biosynthesis of indole alkaloids compounds such as tryptophane decarboxylase, strictosidine synthase, strictosidine glycosidase, dehydrogeissosshizine oxidoreductase, polyneuridine aldehyde esterase, sarpagine bridge enzyme, vinorine reductase, vinorine synthase, vinorine hydroxylase, 17-O-acetylajmalan acetylesterase, or norajamaline N-methyl transferase. In other embodiments, a heterologous nucleic acid encodes an enzyme involved in biosynthesis of vinblastine, vincristine and compounds derived from them, such as tabersonine 16-hydroxylase, 16-hydroxytabersonine 16-O-methyl transferase, desacetoxyvindoline 4-hydroxylase, or desacetylvindoline O-acetyltransferase.

In some embodiments, a heterologous nucleic acid encodes an enzyme involved in biosynthesis of pyridine, tropane, and/or pyrrolizidine alkaloids such as arginine decarboxylase, spermidine synthase, ornithine decarboxylase, putrescine N-methyl transferase, tropinone reductase, hyoscyamine 6-beta-hydroxylase, diamine oxidase, and tropinone dehydrogenase.

A nucleic acid construct may include a heterologous nucleic acid that is transcribed into RNA. Such an RNA can be useful for inhibiting expression of an endogenous gene. Suitable constructs from which such an RNA can be transcribed include antisense constructs. Antisense nucleic acid constructs can include a regulatory region of the invention operably linked, in antisense orientation, to a nucleic acid molecule that is heterologous to the regulatory element. Thus, for example, a transcription product can be similar or identical to the sense coding sequence of an endogenous polypeptide, but transcribed into a mRNA that is unpolyadenylated, lacks a 5' cap structure, or contains an unsplicable intron. Constructs containing operably linked nucleic acid molecules in sense orientation can be used to inhibit the expression of a gene. Methods of co-suppression using a full-length cDNA sequence as well as a partial cDNA sequence are known in the art. See, e.g., U.S. Pat. No. 5,231,020.

Alternatively, a heterologous nucleic acid can be transcribed into a ribozyme. See, U.S. Pat. No. 6,423,885. Heterologous nucleic acid molecules can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contain a 5'-UG-3' nucleotide sequence. The construction and production of hammerhead ribozymes is known in the art. See, for example, U.S. Pat. No. 5,254,678. Hammerhead ribozyme sequences can be embedded in a stable RNA such as a transfer RNA (tRNA) to increase cleavage efficiency in vivo. Perriman, R. et al., *Proc. Natl. Acad. Sci. USA*, 92(13):6175-6179 (1995); de Feyter, R. and Gaudron, J., *Methods in Molecular Biology*, Vol. 74, Chapter 43, "Expressing Ribozymes in Plants," Edited by Turner, P. C., Humana Press Inc., Totowa, N.J. RNA endoribonucleases such as the one that occurs naturally in *Tetrahymena thermophila,* and which have been described extensively by Cech and collaborators can be useful. See, for example, U.S. Pat. No. 4,987,071.

A nucleic acid construct also may include a heterologous nucleic acid that is transcribed into an interfering RNA. See, e.g., U.S. Pat. No. 6,753,139; U.S. Patent Publication 20040053876; and U.S. Patent Publication 20030175783. RNA interference is a cellular mechanism to regulate the expression of genes and the replication of viruses, involving 21-23 nucleotide small interfering RNAs, and 19-21 bp duplexes with 2 nucleotide 3' overhangs. Methods for designing and preparing siRNAs to target a target mRNA are known to those of skill in the art; see, e.g., WO 99/32619 and WO 01/75164. siRNAs with 30-50% GC content typically are more active than those with a higher G/C content. Stretches of greater than 4 T's or A's in the target sequence typically are avoided when selecting an interfering RNA sequence. It may be useful to compare the potential target sites to the appropriate genome database and eliminate from consideration any target sequences with more than 16-17 contiguous base pairs of identity to other coding sequences that are not of interest.

Such an RNA can be one that anneals to another RNA to form an interfering RNA. Such an RNA can also be one that can anneal to itself, e.g., a double stranded RNA having a stem-loop structure. One strand of the stem portion of a double stranded RNA can comprise a sequence that is similar or identical to the sense coding sequence of an endogenous polypeptide, and that is from about 10 nucleotides to about 2,500 nucleotides in length. In some embodiments, the stem portion is similar or identical to UTR sequences 5' of the coding sequence. In some embodiments, the stem portion is similar or identical to UTR sequences 3' of the coding sequence. The length of the sequence that is similar or identical to the sense coding sequence, the 5' UTR, or the 3' UTR can be from 10 nucleotides to 50 nucleotides, from 10 nucleotides to 500 nucleotides, from 15 nucleotides to 300 nucleotides, from 20 nucleotides to 100 nucleotides, or from 25 nucleotides to 100 nucleotides. In some embodiments the length of the sequence that is similar or identical to the sense coding sequence, the 5' UTR, or the 3' UTR can be from 25 nucleotides to 500 nucleotides, from 25 nucleotides to 300 nucleotides, from 25 nucleotides to 1,000 nucleotides, from 100 nucleotides to 2,000 nucleotides, from 300 nucleotides to 2,500 nucleotides, from 200 nucleotides to 500 nucleotides, from 1,000 nucleotides to 2,500 nucleotides, or from 200 nucleotides to 1,000 nucleotides. The other strand of the stem portion of a double stranded RNA can comprise an antisense sequence of an endogenous polypeptide, and can have a length that is shorter, the same as, or longer than the length of the corresponding sense sequence. The loop portion of a double stranded RNA can be from 10 nucleotides to 2,500 nucleotides in length, e.g., from 15 nucleotides to 100 nucleotides, from 20 nucleotides to 300 nucleotides, from 25 nucleotides to 400 nucleotides in length, or from 30 to 2,000 nucleotides. The loop portion of the RNA can include an intron. See, e.g., WO 98/53083; WO 99/32619; WO 98/36083; WO 99/53050; and US patent publications 20040214330 and 20030180945. See also, U.S. Pat. Nos. 5,034,323; 6,452,067; 6,777,588; 6,573,099; and 6,326,527.

A suitable interfering RNA also can be constructed as described in Brummell, et al., *Plant J.* 33:793-800 (2003).

If desired, a nucleic acid construct further can include a 3' untranslated region (3' UTR), which can increase stability of a transcribed sequence by providing for the addition of multiple adenylate ribonucleotides at the 3' end of the transcribed mRNA sequence. A 3' UTR can be, without limitation, the nopaline synthase (NOS) 3' UTR or the 3' UTR of an alkaloid biosynthesis gene, which in a naturally-occurring genome is located 3' of an alkaloid biosynthesis coding region. A nucleic acid construct also can contain inducible elements, intron sequences, enhancer sequences, insulator sequences, or targeting sequences other than those present in a regulatory region described herein. Such other elements may affect expression, or allow a transcript or polypeptide to be targeted to a particular organelle (e.g., a plastid). For example, the 5'-UTR of the small subunit of ribulose bisphosphate carboxylase can be included for enhanced expression. In another example, a nucleic acid encoding a transit peptide from the small subunit of ribulose bisphosphate carboxylase or other plastid targeted proteins can be used to target the encoded product to the plastid. See, for example, U.S. Pat. No. 5,925,806; and Tingey et al., *J. Biol. Chem.,* 1988, 263(20):9651-9657. Regulatory regions and other nucleic acids can be incorporated into a nucleic acid construct using methods known in the art.

A nucleic acid construct may contain more than one regulatory region, each regulatory region operably linked to a heterologous nucleic acid. For example, a nucleic acid construct may contain two regulatory regions, each operably linked to a different heterologous nucleic acid. The two regulatory regions in such a construct can be the same, or can be a different one of the regulatory regions described herein.

Transgenic Plants and Cells

Transgenic plants and cells can be obtained by introducing at least one nucleic acid construct described herein. Suitable plants for transformation include dicots such as cotton, safflower, alfalfa, soybean, rapeseed (high erucic acid and canola), guayule, or sunflower. Also suitable are monocots such as corn, wheat, rye, barley, oat, rice, millet, amaranth or sorghum. Also suitable are vegetable crops or root crops such as broccoli, peas, sweet corn, popcorn, tomato, beans (including kidney beans, lima beans, dry beans, green beans) and the like. Also suitable are fruit crops such as peach, pear, apple, cherry, orange, lemon, grapefruit, plum, mango and palm. Other suitable species include *Lycopersicum esculentum, Nicotiana* spp. (e.g., *Nicotiana tabacum*), *Capsicum* spp. (including *C. annuum*), *Parthenium argentatum* Gray, *Mentha spicata, M. pulegium, M. piperita, Thymus vulgaris* L., *Origanum vulgare, Rosmarinus officinalis, Melissa officinalis, Lavandula augustifolia* or *Salvia officinalis*. Other suitable species include *Hevea benthamiana, Hevea guianensus, Hevea brasiliensis, Manihot glaziovii, Manihot dichotoma, Castilla elastica, Ficus elastica, Funtimia elastica, Landolphia kirkii, Landolphia gentilli, Landolphia heudelotii, Landolphia owariensis, Crytostegia grandiflora, Crytostegia madagascariansis, Taraxacum megalorhizon, Palaquim gutta, Manilkara bidentata,* and *Manilkara zapata*.

Thus, the regulatory regions described herein can be utilized with dicotyledonous plants belonging to the orders Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, Santales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales. Regulatory regions described herein can also be utilized with monocotyledonous plants belonging to the orders Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchidales, or with plants belonging to Gymnospermae, e.g., Pinales, Ginkgoales, Cycadales and Gnetales.

Thus, the invention has use over a broad range of plant species, including species from the genera *Allium, Alseodaphne, Anacardium, Arachis, Asparagus, Atropa, Avena, Beilschmiedia, Brassica, Citrus, Citrullus, Capsicum, Catharanthus, Carthamus, Cocculus, Cocos, Coffea, Croton, Cucumis, Cucurbita, Daucus, Duguetia, Elaeis, Eschscholzia, Ficus, Fragaria, Glaucium, Glycine, Gossypium, Helianthus, Heterocallis, Hevea, Hordeum, Hyoscyamus, Lactuca, Landolphia, Linum, Litsea, Lolium, Lupinus, Lycopersicon, Malus, Manihot, Majorana, Medicago, Musa, Nicotiana, Olea, Oryza, Panicum, Pannesetum, Papaver, Parthenium, Persea, Phaseolus, Pinus, Pistachia, Pisum, Pyrus, Prunus, Raphanus, Rhizocarya, Ricinus, Secale, Senecio, Sinomenium, Sinapis, Solanum, Sorghum, Stephania, Theobroma, Trigonella, Triticum, Vicia, Vinca, Vitis, Vigna* and *Zea*.

A particularly suitable group of species with which to practice the invention include alkaloid producing plants, e.g., plants from the *Papaveraceae*, Berberidaceae, Lauraceae, Menispermaceae, Euphorbiaceae, Leguminosae, Boraginaceae, Apocynaceae, Asclepiadaceae, Liliaceae, Gnetaceae, Erythroxylaceae, Convolvulaceae, Ranunculaeceae, Rubiaceae, Solanaceae, and Rutaceae families. The *Papaveraceae* family, for example, contains about 250 species found mainly in the northern temperate regions of the world and includes plants such as California poppy and Opium poppy. Useful genera within the *Papaveraceae* family include the *Papaver* (e.g., *Papaver bracteatum, Papaver orientale, Papaver setigerum,* and *Papaver somniferum*), *Sanguinaria, Dendromecon, Glaucium, Meconopsis, Chelidonium, Eschscholzioideae* (e.g., *Eschscholzia, Eschscholzia californica*), and *Argemone* (e.g., *Argemone hispida, Argemone mexicana,* and *Argemone munita*) genera. Other alkaloid producing species with which to practice this invention include *Croton salutaris, Croton balsamifera, Sinomenium acutum, Stephania cepharantha, Stephania zippeliana, Litsea sebiferea, Alseodaphne perakensis, Cocculus laurifolius, Duguetia obovata, Rhizocarya racemifera,* and *Beilschmiedia oreophila*.

Seeds produced by a transgenic plant can be grown and selfed (or outcrossed and selfed) to obtain plants homozygous for the construct. Seeds can be analyzed to identify those homozygotes having the desired expression of the construct. Transgenic plants can be entered into a breeding program, e.g., to increase seed, to introgress the novel construct into other lines or species, or for further selection of other desirable traits. Alternatively, transgenic plants can be obtained by vegetative propagation of a transformed plant cell, for those species amenable to such techniques.

As used herein, a transgenic plant also refers to progeny of an initial transgenic plant. Progeny includes descendants of a particular plant or plant line, e.g., seeds developed on an instant plant. Progeny of an instant plant also includes seeds formed on $F_1$, $F_2$, $F_3$, and subsequent generation plants, or seeds formed on $BC_1$, $BC_2$, $BC_3$, and subsequent generation plants.

Transgenic techniques for introducing nucleic acid into plants include, without limitation, *Agrobacterium*-mediated transformation, electroporation, and particle gun transformation. Illustrative examples of transformation techniques are described in PCT Application No. 99/04117 (particle bombardment of Brassica) and U.S. Pat. No. 5,188,958 (*Agrobacterium*). See also, *Nature Biotechnology* 22(12): 1559-1566 (2004); *Funct. Plant Biol.* 30:1045-1058 (2000); and Park et al., *J. Exp. Botany* 51(347):1005-1016 (2003). Transformation methods utilizing the Ti and Ri plasmids of *Agrobacterium* spp. typically use binary type vectors. If cell or tissue cultures are used as the recipient tissue for transformation, plants can be regenerated from transformed cultures by techniques known to those skilled in the art.

Transgenic plants can be useful for a variety of purposes, since a regulatory region disclosed herein can be used to express any of a number of desired heterologous nucleic acids. Plant cell cultures also can be utilized in the same manner. For example, the amount of an enzyme or a regulatory protein involved in biosynthesis of alkaloid compounds can be modulated using the methods and compositions described herein, leading to a modulation in the amount of one or more alkaloid compounds in the transgenic plant relative to a control plant that lacks the recombinant nucleic acid construct. Alkaloid compounds that can be modulated include tetrahydrobenzylisoquinoline alkaloids, morphinan alkaloids, benzophenanthridine alkaloids, monoterpenoid indole alkaloids, bisbenzylisoquinoline alkaloids, pyridine alkaloids, purine alkaloids, tropane alkaloids, quinoline alkaloids, terpenoid alkaloids, betaine alkaloids, steroid alkaloids, acridone alkaloids, and phenethylamine alkaloids.

The invention will be further described in the following examples, which do not limit the scope of the invention described in the claims.

EXAMPLES

Example 1

Isolation of *Papaveraceae* Regulatory Regions

To clone the regulatory regions PsHMCOMT2 (SEQ ID NO:3) and PsCRX (SEQ ID NO:5), a genomic library was constructed from opium poppy genomic DNA that was partially digested with restriction enzyme Sau3A. A thermal asymmetric interlaced (TAIL)-PCR reaction was performed following the protocol published by Liu et al. (1995) *Plant J.*, 8:457-63, with some modifications. A mixture of an arbitrary set of forward primers, designated AD2 (5'-NGTC-GASWGANAWGAA-3', with S=G or C, W=A or T, and N=A, G, C, or T; SEQ ID NO:19), was used in combination with a reverse primer specific to the reported cDNA sequence of interest. The reverse primers were designed such that they anneal to the 5'-end region of the cDNA of interest based on the reported sequence (for PsHMCOMT2, see gi|33413893; for PsCRX, see gi|6478215). For regulatory region PsHMCOMT2, the reverse primers used were Ps-HMCOMT2-PR3 (5'-GATGGAAACTTCTTGTGTTG-CAGCA-3'; SEQ ID NO:32) and Ps-HMCOMT2-PR2 (5'-GCATCTAAACTACCCATTAGATATGCGA-3'; SEQ ID NO:33). For regulatory region PsCRX, the reverse primers used were Ps-CR-PR3 (5'-CTGTATCGAAGTGTC-TATAACCCACCTCT-3'; SEQ ID NO:16) and Ps-CR-PR2 (5'-CCAATTTCACTCTTTCAGACCCTTGA-3'; SEQ ID NO:17). After the first round of TAIL-PCR using AD2 primers and the PR3 primer for the targeted regulatory region, a 1-µl aliquot of the PCR product was used to perform the second round of amplification using the AD2 primers and the PR2 primer for the targeted regulatory region. The amplification product of the second round PCR reaction was separated by agarose gel electrophoresis to isolate DNA bands of desired length and intensity. The bands were isolated from the gel using a Qiagen DNA purification kit. The isolated DNA products were ligated to the pCR2.1-Topo vector (Invitrogen) for cloning and subsequent sequencing.

To clone the regulatory region EcNMCH3 (SEQ ID NO:1), genomic DNA of *Eschscholzia californica* was digested with restriction enzymes XbaI and NheI prior to ligation to a linker/adaptor consisting of a top strand (5'-GGCCCGGGCTGCGATCATCAAGGAAG-TAAGCGTGGTCGACGGCCCGGGCTGC -3'; SEQ ID NO:20) and a shorter complementary bottom strand (5'-P-CTAGGCAGCCCGGGCCGTCGACCAC-NH2-3'; SEQ ID NO:21). The GATC 5'-overhang of the linker/adaptor is compatible with the overhangs of the genomic fragments resulting from XbaI and NheI digestion. A first round of PCR amplification was performed using the YES3-5 primer (5'-GATCATCAAGGAAGTAA-3'; SEQ ID NO:22), which anneals to the linker/adaptor, and the Ec-NMCH3-PR1 primer (5'-GAGGAGGATGGGCTTCTCCATA-3'; SEQ ID NO:23), which is specific to the coding region of the NMCH3 gene based on the reported sequence (gi|3127030). The PCR product was diluted one hundred-fold, and a 1-µl aliquot was used to perform the second round of PCR using the NAP2 primer (5'-TCGACGGCCCGGGCTGCCTAG-3'; SEQ ID NO:24) and the Ec-NMCH3-PR2 primer (5'-AGC-TACCTGATATTCTTGGGAGGAGA-3'; SEQ ID NO:25), which is specific to the 5' untranslated region of the NMCH3 gene. The PCR products were separated by agarose gel electrophoresis, and desired DNA bands were isolated as described above. The isolated DNA products were ligated to the pCR2.1-Topo vector (Invitrogen) for cloning and subsequent sequencing.

To clone the regulatory regions PsROMT (SEQ ID NO:2), PsSAT (SEQ ID NO:4), and PsCR3 (SEQ ID NO:6), a genomic library was constructed from opium poppy genomic DNA that was partially digested with restriction enzyme Sau3A. The genomic fragments were ligated to the BamHI site of the pZeroBackground vector (Invitrogen). To amplify the desired DNA fragment corresponding to the regulatory regions PsROMT, PsSAT, and PsCR3, PCR amplification was performed using either the M13-F forward primer (5'-GTAAAACGACGGCCAG-3'; SEQ ID NO:26) or the M13-R reverse primer (5'-CAGGAAACAGCTAT-GAC-3'; SEQ ID NO:27) in combination with reverse primers specific to the 5' end region of the cDNA sequence of interest. The reverse primers were designed such that they anneal towards the 5'-end region of the cDNA of interest based on the reported sequence (for PsROMT, see gi|33286371; for PsSAT, see gi|14861416; for PsCR3, see gi|6478215). For regulatory region PsROMT, the specific reverse primers used were Ps-ROMT-PR3 (5'-CCAT-TGAATCCACGAATGCGA-3'; SEQ ID NO:28) and Ps-ROMT-PR2 (5'-GCTTGCCCTTTCAACCTTTCTTCT-3'; SEQ ID NO:29). For regulatory region PsSAT, the specific reverse primers used were Ps-SAT-PR3 (5'-GGAGT-TGTGGGTTTAATGGTTTCCT-3'; SEQ ID NO:30) and Ps-SAT-PR2 (5'-ATCACTTCAACAGCAGCACTATACAT-TGT-3'; SEQ ID NO:31). For regulatory region PsCR3, the specific reverse primers used were Ps-CR-PR3 (5'-CTG-TATCGAAGTGTCTATAACCCACCTCT-3'; SEQ ID NO:16), Ps-CR-PR2 (5'-CCAATTTCACTCTTTCAGAC-CCTTGA-3'; SEQ ID NO:17), and Ps-CR-PR1 (5'-CAGG-TACACCACCGATCTCCATTCT-3'; SEQ ID NO:18). The first round of PCR amplification was performed using the PR3 set of primers in combination with either M13-F or M13-R. An aliquot of the PCR product was electrophoresed in an agarose gel to qualitatively determine which of the M13 primers was producing a desirable product. The second round of amplification was performed using a 1-µl aliquot of the remaining first-round PCR reaction with the PR2 set of primers in combination with the positive M13 primer. The PCR products were separated by agarose gel electrophoresis, and desired DNA bands were isolated as described above. The isolated DNA products were ligated to the pCR2.1-Topo vector (Invitrogen) for cloning and subsequent sequencing.

The regulatory regions EcBBE and PsBBE also were cloned using PCR. The regulatory region EcBBE refers to nucleotides 435 to 1504 of a California poppy BBE1 gene (gi|2897943). The regulatory region PsBBE refers to nucleotides 1644 to 2649 of an opium poppy BBE1 gene (gi|3282516).

Genomic DNAs were isolated using the Qiagen DNA Isolation Kit from leaf tissues collected from plants of *Eschscholzia californica* (Source: Thompson and Morgan, Jackson, N.J.) and *Papaver somniferum* cv. Bea's Choice (Source: The Basement Shaman, Woodstock, Ill.).

Standard molecular biology techniques were used to generate a set of T-DNA binary vector constructs containing regulatory regions described above operably linked to luciferase coding sequences. Each construct also contained a gene conferring resistance to the herbicide Finale®. The constructs were introduced into *Agrobacterium*. Each *Agrobacterium* transformant was grown in an incubator-shaker at 28° C. in 150 µl of YEB broth containing 100 µg/mL spectinomycin, 50 µg/mL rifampicin, and 20 µM acetosyringone. The *Agrobacterium* cells were harvested by centrifugation at 4,000 rpm for at least 25 minutes. The supernatant was discarded, and each pellet was resuspended in a solution of 10 mM MgCl; 10 mM MES, pH 5.7; and 150 µM acetosyringone to an optical density ($OD_{600}$) of about 0.05 to 0.1.

Example 2

Generation and Analysis of *Papaver somniferum* Leaf Disks Containing Alkaloid Regulatory Region::Luciferase Constructs Leaf disks were prepared from wild-type *Papaver somniferum* plants using a paper puncher. The leaf disks were infected with *Agrobacteria* containing constructs including regulatory regions operably linked to luciferase coding sequences, as described in Example 1. Infection was performed by immersing the leaf disks in about 5 to 10 mL of a suspension of *Agrobacterium* culture for about 2 min. The treated leaf disks were quickly blot-dried in tissue paper and transferred to a plate lined with paper towels wetted with 1X MS solution (adjusted to pH 5.7 with 1 N KOH and supplemented with 1 mg/L BAP and 0.25 mg/L NAA). The leaf disks were incubated in a growth chamber under a long-day light/dark cycle at 22° C. for 5 days prior to analysis.

Additional leaf disks from wild-type *Papaver somniferum* plants were infected with *Agrobacterium* containing a binary construct comprising a CaMV 35S constitutive promoter operably linked to a luciferase reporter coding sequence. These leaf disks were used as positive controls to indicate that the method of *Agrobacterium* infection was working. Separate leaf disks were transiently infected with *Agrobacterium* containing a binary construct including a CaMV 35S promoter operably linked to a GFP coding sequence. These leaf disks served as reference controls to indicate that the luciferase reporter activity in the treated disks was not merely a response to treatment with *Agrobacterium*.

Treated leaf disks were collected five days after infection and placed in a square Petri dish. Each leaf disk was sprayed with 10 μM luciferin in 0.01% Triton X-100. Leaves were then incubated in the dark for at least a minute prior to imaging with a Night Owl™ CCD camera from Berthold Technology.

Expression of the luciferase reporter gene was detected in leaf disks transformed with a construct containing the PsCRX, PsHMCOMT2, PsCR3, or CaMV 35S regulatory region operably linked to a luciferase coding sequence. Luciferase expression was also detected in leaf disks transformed with a construct containing the EcNMCH3 and EcBBE regulatory regions, each operably linked to a luciferase coding sequence. However, no luciferase expression was detected in leaf disks transformed with the PsBBE regulatory region operably linked to a luciferase coding sequence, or in leaf disks transformed with the PsROMT or PsSAT regulatory region operably linked to a luciferase coding sequence.

Example 3

Generation of *Nicotiana* Plants Containing Alkaloid Regulatory Region::Luciferase Constructs and Regulatory Protein Constructs Stable *Nicotiana tabacum* screening lines were generated by transforming *Nicotiana* leaf explants with T-DNA binary vector constructs containing regulatory regions described in Example 1 operably linked to luciferase coding sequences. The transformation was performed essentially as described by Rogers et al., *Methods in Enzymology* 118:627 (1987).

Leaf disks were cut from leaves of the screening lines using a paper puncher. The leaf disks were transiently infected with *Agrobacterium* clones containing T-DNA binary vector constructs comprising a CaMV 35S promoter operably linked to a coding sequence for one of the regulatory proteins listed in Table 1. Transient infection of the leaf disks was performed as described in Example 2.

As controls, leaf disks from wild-type *Nicotiana tabacum* plants were transiently infected with *Agrobacteria* containing a binary vector comprising a CaMV 35S promoter operably linked to a luciferase reporter coding sequence. These leaf disks were used as positive controls to indicate that the method of *Agrobacterium* infection was working. Some leaf disks from *Nicotiana* screening plants were transiently infected with *Agrobacteria* containing a binary construct of a CaMV 35S promoter operably linked to a GFP coding sequence. These leaf disks served as reference controls to indicate that the luciferase reporter activity in the treated disks was not merely a response to treatment with *Agrobacterium*.

Treated leaf disks were collected five days after infection and placed in a square Petri dish. Each leaf was sprayed with 10 μM luciferin in 0.01% Triton X-100. Leaves were then incubated in the dark for at least one minute prior to imaging with a Night Owl™ CCD camera from Berthold Technology. The exposure time depended on the screening line being tested. In most cases, the exposure time was between 2 and 5 minutes. Qualitative scoring of luciferase reporter activity from each infected leaf was preformed by visual inspection and comparison of images, taking into account the following criteria: (1) if the luminescence signal was higher in the treated leaf than in the 35S-GFP-treated reference control (considered as the background activity of the regulatory region), and (2) if the first criterion occurred in at least two independent transformation events carrying the regulatory region-luciferase reporter construct. Examples of regulatory proteins that were observed to transiently transactivate alkaloid regulatory regions are listed in Table 1.

TABLE 1

Combinations of regulatory regions and regulatory proteins producing expression of a reporter gene operably linked to each regulatory region

| Regulatory Region | Regulatory Protein SEQ ID NO: | Regulatory Protein Gemini_ID | Regulatory Protein cDNA_ID | Screening Organism |
|---|---|---|---|---|
| PsHMCOMT2-L | 10 | 5110C8 | 23655935 | Tobacco |
| PsHMCOMT2-L | 34 | 5110C9 | 23660631 | Tobacco |
| PsHMCOMT2-L | 11 | 555A1 | 23388445 | Tobacco |
| PsROMT-L | 7 | 531H6 | 23427553 | Tobacco |
| PsROMT-L | 9 | 531H9 | 23447935 | Tobacco |
| PsROMT-L | 8 | 531G11 | 23395214 | Tobacco |
| PsSAT-L | 12 | 552G1 | 23777863 | Tobacco |
| EcBBE-L-EcNMCH3-L | 13 | 555A3 | 23377122 | Tobacco |
| EcBBE-L-EcNMCH3-L | 14 | 555C4 | 23704869 | Tobacco |
| EcBBE-L-EcNMCH3-L | 15 | Zap1 | 23468313 | Tobacco |

Legend:
L = Luciferase
EcBBE = *Eschscholzia californica* berberine bridge enzyme gene promoter
EcNMCH3 = *Eschscholzia californica* N-methylcoclaurine 3'-hydroxylase gene promoter
PsHMCOMT2 = *Papaver somniferum* hydroxy N-methyl S-coclaurine 4-O-methyltransferase 2 gene promoter
PsROMT = *Papaver somniferum* (R,S)-reticuline 7-O-methyltransferase gene promoter
PsSAT = *Papaver somniferum* (7S)-salutaridinol 7-O-acetyltransferase gene promoter

What is claimed is:

1. An isolated polynucleotide comprising SEQ ID NO:6.

2. A nucleic acid construct comprising the nucleotide sequence set forth in SEQ ID NO:6 operably linked to a heterologous nucleic acid.

3. The nucleic acid construct of claim 2, wherein said heterologous nucleic acid encodes a polypeptide.

4. A transgenic *Papaveraceae* plant or plant cell, said plant or plant cell comprising at least one nucleic acid construct, said construct comprising the nucleotide sequence set forth in SEQ ID NO:6 operably linked to a heterologous nucleic acid.

5. A transgenic *Papaveraceae* plant or plant cell, wherein said plant or plant cell comprising first and second nucleic acid constructs, each said construct comprising the nucleotide sequence set forth in SEQ ID NO:6 operably linked to a heterologous nucleic acid.

6. The transgenic *Papaveraceae* plant or cell of claim 4 or claim 5, wherein said plant or cell is a plant.

7. A transgenic *Papaveraceae* seed from a transgenic plant, said plant comprising at least one nucleic acid construct, said construct comprising the nucleotide sequence set forth in SEQ ID NO:6 operably linked to a heterologous nucleic acid.

8. The transgenic *Papaveraceae* plant or cell of claim 4, wherein said heterologous nucleic acid encodes a regulatory protein involved in alkaloid biosynthesis.

9. The transgenic *Papaveraceae* plant or cell of claim 4, wherein said heterologous nucleic acid encodes an enzyme involved in alkaloid biosynthesis.

10. The transgenic *Papaveraceae* plant or cell of claim 8, wherein said heterologous nucleic acid encodes an enzyme selected from the group consisting of salutaridinol 7-O-acetyltransferase, salutaridine synthase, salutaridine reductase, morphine 6-dehydrogenase; and codeinone reductase.

11. The transgenic *Papaveraceae* plant or cell of claim 4, wherein said heterologous nucleic acid is transcribed into an interfering RNA against a protein involved in alkaloid biosynthesis.

12. A transgenic *Papaveraceae* seed from a transgenic plant, said plant comprising first and second nucleic acid constructs, each said construct comprising the nucleotide sequence set forth in SEQ ID NO:6 operably linked to a heterologous nucleic acid.

13. A transgenic *Papaveraceae* seed from a transgenic plant, said plant comprising first and second nucleic acid constructs, wherein said first nucleic acid construct comprises the nucleotide sequence set forth in SEQ ID NO:6 operably linked to a heterologous nucleic acid.

* * * * *